(12) United States Patent
Kamon

(10) Patent No.: US 12,020,808 B2
(45) Date of Patent: Jun. 25, 2024

(54) MEDICAL IMAGE PROCESSING APPARATUS, MEDICAL IMAGE PROCESSING METHOD, PROGRAM, AND DIAGNOSIS SUPPORT APPARATUS

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 487 days.

(21) Appl. No.: 17/229,966

(22) Filed: Apr. 14, 2021

(65) Prior Publication Data

US 2021/0233648 A1 Jul. 29, 2021

Related U.S. Application Data

(63) Continuation of application No. PCT/JP2019/042158, filed on Oct. 28, 2019.

(30) Foreign Application Priority Data

Nov. 1, 2018 (JP) .................. 2018-206758

(51) Int. Cl.
G16H 30/40 (2018.01)
A61B 6/46 (2024.01)
G16H 15/00 (2018.01)

(52) U.S. Cl.
CPC ............. *G16H 30/40* (2018.01); *A61B 6/463* (2013.01); *G16H 15/00* (2018.01)

(58) Field of Classification Search
CPC ........ G16H 30/40; G16H 15/00; G16H 20/40; G16H 30/20; G16H 50/70; A61B 6/463; A61B 1/045; H04N 7/18

(Continued)

(56) References Cited

U.S. PATENT DOCUMENTS 7,298,878 B2 * 11/2007 Goto ...................... A61B 6/463
382/128
8,189,888 B2 5/2012 Takahashi
(Continued)

FOREIGN PATENT DOCUMENTS

CN 103491851 A 1/2014
EP 2 517 614 A1 10/2012
(Continued)

OTHER PUBLICATIONS

The extended European search report issued by the European Patent Office dated Sep. 20, 2021, which corresponds to European Patent Application No. 19878049.6-1122 and is related to U.S. Appl. No. 17/229,966.

(Continued)

*Primary Examiner* — Jerome Grant, II
(74) *Attorney, Agent, or Firm* — Studebaker & Brackett PC

(57) ABSTRACT

Provided are a medical image processing apparatus, a medical image processing method, a program, and a diagnosis support apparatus that appropriately control whether or not to report reporting information of a medical image independently of a user operation. The above object is achieved by a medical image processing apparatus including a reporting control unit that performs control to bring reporting information included in a medical image into either a reporting state in which the reporting information is reported by a reporting unit or a non-reporting state in which the reporting information is not reported by the reporting unit. The reporting control unit brings the reporting information into the non-reporting state in a case where the medical image satisfies a non-reporting condition and brings the reporting information into the reporting state after a non-reporting (Continued)

time has elapsed from when the medical image does not satisfy the non-reporting condition.

17 Claims, 17 Drawing Sheets

(58) Field of Classification Search
USPC .................................................. 382/128
See application file for complete search history.

(56) References Cited

U.S. PATENT DOCUMENTS

| | | | |
|---|---|---|---|
| 2003/0179915 A1 | 9/2003 | Goto | |
| 2009/0087049 A1 | 4/2009 | Takahashi | |
| 2012/0274754 A1 | 11/2012 | Tsuruoka | |
| 2012/0287238 A1 | 11/2012 | Onishi et al. | |
| 2013/0155216 A1 | 6/2013 | Kasumi | |
| 2014/0132268 A1 | 5/2014 | Nagao et al. | |
| 2017/0073337 A1* | 3/2017 | Kusakabe | ............ C07D 413/12 |
| 2019/0313883 A1 | 10/2019 | Hosoya et al. | |

FOREIGN PATENT DOCUMENTS

| | | |
|---|---|---|
| JP | H11-104064 A | 4/1999 |
| JP | 2002-325761 A | 11/2002 |
| JP | 4393016 B2 | 1/2010 |
| JP | 2011-255006 A | 12/2011 |
| JP | 2013-162874 A | 8/2013 |
| JP | 2016-062488 A | 4/2016 |
| JP | 2017-086688 A | 5/2017 |
| WO | 2011/096279 A1 | 8/2011 |
| WO | 2012/101888 A1 | 8/2012 |
| WO | 2012/176886 A1 | 12/2012 |
| WO | 2017/073337 A1 | 5/2017 |
| WO | 2018/142664 A1 | 8/2018 |
| WO | WO2019012586 * 1/2019 ............ A61B 1/045 |  |

OTHER PUBLICATIONS

An Office Action; "Notice of Reasons for Refusal," mailed by the Japanese Patent Office dated Feb. 17, 2023, which corresponds to Japanese Patent Application No. 2020-553886 and is related to U.S. Appl. No. 17/229,966; with English language translation.

International Search Report issued in PCT/JP2019/042158; dated Jan. 21, 2020.

International Preliminary Report on Patentability and Written Opinion issued in PCT/JP2019/042158; dated Apr. 27, 2021.

An Office Action; "Notice of Reasons for Refusal," mailed by the Japanese Patent Office dated Sep. 30, 2022, which corresponds to Japanese Patent Application No. 2020-553886 and is related to U.S. Appl. No. 17/229,966; with English language translation.

An Office Action mailed by China National Intellectual Property Administration dated Sep. 22, 2023, which corresponds to Chinese Patent Application and is related to U.S. Appl. No. 17/229,966; with English language translation.

An Office Action mailed by China National Intellectual Property Administration on Mar. 22, 2024, which corresponds to Chinese Patent Application No. 201980072091.0 and is related to U.S. Appl. No. 17/229,966; with English language translation.

* cited by examiner

MEDICAL IMAGE PROCESSING APPARATUS, MEDICAL IMAGE PROCESSING METHOD, PROGRAM, AND DIAGNOSIS SUPPORT APPARATUS

CROSS-REFERENCE TO RELATED APPLICATIONS

The present application is a Continuation of PCT International Application No. PCT/JP2019/042158 filed on Oct. 28, 2019 claiming priority under 35 U.S.C § 119(a) to Japanese Patent Application No. 2018-206758 filed on Nov. 1, 2018. Each of the above applications is hereby expressly incorporated by reference, in its entirety, into the present application.

BACKGROUND OF THE INVENTION

1. Field of the Invention

The present invention relates to a medical image processing apparatus, a medical image processing method, a program, and a diagnosis support apparatus, and specifically relates to a technique of controlling whether or not to report reporting information of a medical image.

2. Description of the Related Art

A technique of automatically detecting a region of interest, such as a lesion, from an endoscopic image is expected to contribute to preventing oversight of a lesion. The automatic detection technique is merely directed to preventing oversight, and continuously reporting a detection result after a user has recognized the presence of a lesion hinders observation and is thus not preferable. Thus, after the recognition by the user, reporting information may be intentionally brought into a non-reporting state of not being reported.

However, the user may continue an examination while not recognizing that a non-reporting state has started. In this case, reporting information is not reported to the user, and thus a lesion may be overlooked.

To address such an issue, JP4393016B discloses a technique of hiding a marker (corresponding to reporting information) for a candidate lesion shadow added to a computed tomography (CT) image in response to a click on a hide icon, and regenerating a CT image with the original marker after a predetermined time has elapsed. This technique makes it possible to, after the marker has been hidden, prevent an examination from being continued with the marker being kept hidden.

SUMMARY OF THE INVENTION

However, the technique described in JP4393016B is disadvantageous in that a user is required to perform an operation to hide a marker.

The present invention has been made in view of these circumstances, and an object of the present invention is to provide a medical image processing apparatus, a medical image processing method, a program, and a diagnosis support apparatus that appropriately control whether or not to report reporting information of a medical image independently of a user operation.

To achieve the above-described object, an aspect of a medical image processing apparatus is a medical image processing apparatus including a reporting control unit that performs control to bring reporting information included in a medical image into either a reporting state in which the reporting information is reported by a reporting unit or a non-reporting state in which the reporting information is not reported by the reporting unit. The reporting control unit brings the reporting information into the non-reporting state in a case where the medical image satisfies a non-reporting condition and brings the reporting information into the reporting state after a non-reporting time has elapsed from when the medical image does not satisfy the non-reporting condition.

According to this aspect, the reporting information is brought into the non-reporting state in a case where the medical image satisfies the non-reporting condition and is brought into the reporting state after the non-reporting time has elapsed from when the medical image does not satisfy the non-reporting condition. Thus, the reporting information is brought into the reporting state in a case where the non-reporting condition is not satisfied, is brought into the non-reporting state in a case where the non-reporting condition is satisfied, is kept in the non-reporting state from when the non-reporting condition is not satisfied to when the non-reporting time elapses, and is brought into the reporting state after the non-reporting time has elapsed. Thus, it is possible to appropriately control whether or not to report reporting information of a medical image independently of a user operation.

Preferably, the medical image processing apparatus includes an image acquiring unit that sequentially acquires frame images of the medical image, a reporting information acquiring unit that acquires the reporting information from the medical image, a determining unit that determines whether or not the medical image satisfies the non-reporting condition, and a time measuring unit that measures a time elapsed from when the medical image does not satisfy the non-reporting condition. Accordingly, it is possible to appropriately perform acquisition of the medical image, acquisition of the reporting information, determination of the non-reporting condition, and determination of the elapsed time.

Preferably, the non-reporting condition is a condition of determining an image feature quantity of the medical image, and the medical image processing apparatus includes an image feature quantity acquiring unit that acquires the image feature quantity from the medical image. Accordingly, it is possible to stop reporting in accordance with the image feature quantity.

Preferably, the image feature quantity includes at least one of a luminance of the medical image, color information of the medical image, a temporal change in the medical image, or frequency information of the medical image. Accordingly, it is possible to appropriately stop reporting.

Preferably, the non-reporting condition is a condition of determining a treatment state of a subject in the medical image, and the medical image processing apparatus includes a treatment state estimating unit that estimates the treatment state from the medical image. Accordingly, it is possible to stop reporting in accordance with the treatment state.

Preferably, the medical image processing apparatus includes a non-reporting time setting unit that sets the non-reporting time in accordance with the treatment state. Accordingly, it is possible to appropriately set the non-reporting time.

Preferably, the non-reporting condition is a condition of determining a region-of-interest feature quantity, and the medical image processing apparatus includes a region-of-interest detecting unit that detects a region of interest from the medical image, and a region-of-interest feature quantity acquiring unit that acquires the region-of-interest feature quantity from the region of interest. Accordingly, it is possible to stop reporting in accordance with the region-of-interest feature quantity.

Preferably, the region-of-interest feature quantity includes at least one of an area of the region of interest, a position of the region of interest in the medical image, or a temporal change in the region of interest. Accordingly, it is possible to appropriately stop reporting.

Preferably, the reporting unit includes a sound output unit that outputs a sound, and the reporting control unit includes a sound control unit that causes the sound output unit to output the sound. Accordingly, it is possible to appropriately report the reporting information.

Preferably, the reporting unit includes a first display unit, and the reporting control unit includes a display control unit that causes the first display unit to display the reporting information. Accordingly, it is possible to appropriately report the reporting information.

Preferably, the reporting unit includes a second display unit different from the first display unit, and the display control unit causes the second display unit to display the reporting information. Accordingly, it is possible to appropriately report the reporting information.

Preferably, the display control unit changes, in accordance with the reporting state and the non-reporting state, a manner in which the second display unit displays the reporting information. Accordingly, it is possible to appropriately report the reporting information.

Preferably, the display control unit causes the second display unit to display the reporting information in a case of the non-reporting state. Accordingly, it is possible to appropriately observe the medical image in the first display unit and to appropriately report the reporting information in the second display unit.

Preferably, the display control unit causes a third display unit different from the first display unit to display information indicating the non-reporting state. Accordingly, a user can know that the reporting information is in the non-reporting state.

Preferably, the display control unit causes a fourth display unit different from the first display unit to display information about a time elapsed from when the medical image does not satisfy the non-reporting condition. Accordingly, a user can know the information about the elapsed time.

To achieve the above-described object, an aspect of a diagnosis support apparatus is a diagnosis support apparatus including the above-described medical image processing apparatus and the first display unit. According to this aspect, it is possible to appropriately control whether or not to display reporting information of a medical image independently of a user operation.

To achieve the above-described object, an aspect of a medical image processing method is a medical image processing method including a reporting control step of performing control to bring reporting information included in a medical image into either a reporting state in which the reporting information is reported by a reporting unit or a non-reporting state in which the reporting information is not reported by the reporting unit. The reporting control step brings the reporting information into the non-reporting state in a case where the medical image satisfies a non-reporting condition and brings the reporting information into the reporting state after a non-reporting time has elapsed from when the medical image does not satisfy the non-reporting condition.

According to this aspect, it is possible to appropriately control whether or not to report reporting information of a medical image independently of a user operation. A program for causing a computer to execute the above-described medical image processing method is also included in this aspect.

According to the present invention, it is possible to appropriately control whether or not to report reporting information of a medical image independently of a user operation.

DESCRIPTION OF THE PREFERRED EMBODIMENTS

Hereinafter, preferred embodiments of the present invention will be described in detail with reference to the attached drawings.

Overall Configuration of Endoscope System

Figure 1:
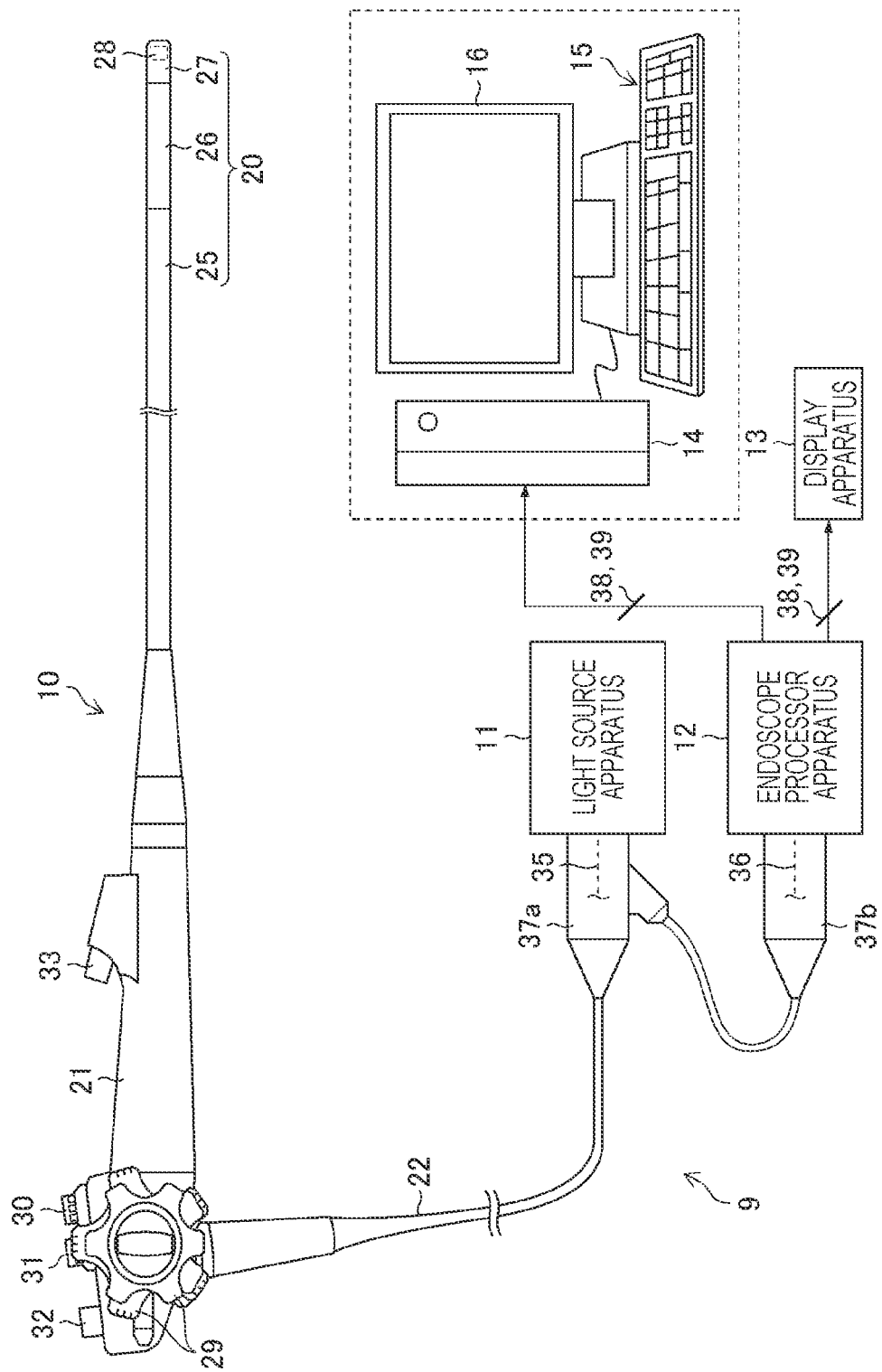
FIG. 1 a schematic diagram illustrating an overall configuration of an endoscope system including a medical image processing apparatus.

FIG. 1 is a schematic diagram illustrating an overall configuration of an endoscope system 9 including a medical image processing apparatus according to the present embodiment. As illustrated in FIG. 1, the endoscope system 9 includes an endoscope 10 which is an electronic endoscope, a light source apparatus 11, an endoscope processor apparatus 12, a display apparatus 13, a medical image processing apparatus 14, an operation unit 15, and a display 16.

The endoscope 10 is for capturing a time-series medical image and is, for example, a soft endoscope. The endoscope 10 has an insertion section 20 that is to be inserted into a subject and that has a distal end and a base end, a handheld operation section 21 that communicates with the base end side of the insertion section 20 and that is to be gripped by a user (medical doctor) to perform various operations, and a universal cord 22 that communicates with the handheld operation section 21.

The insertion section 20 has a small diameter and is elongated as a whole. The insertion section 20 is constituted by a soft part 25 having flexibility, a bending part 26 that can be bent by operating the handheld operation section 21, and a distal end part 27 including therein an imaging optical system (objective lens) that is not illustrated, an imaging device 28, and so forth, which are arranged in this order from the base end side toward the distal end side and communicate with each other.

The imaging device 28 is a complementary metal-oxide semiconductor (CMOS) imaging device or a charge-coupled device (CCD) imaging device. On an imaging surface of the imaging device 28, image light of a portion to be observed is incident through an observation window that is open in a distal end surface of the distal end part 27 and that is not illustrated, and an objective lens that is disposed behind the observation window and that is not illustrated. The imaging device 28 captures the image light of the portion to be observed that has been incident on the imaging surface (converts the image light into an electric signal) and outputs an image signal.

The handheld operation section 21 is provided with various operation members that are to be operated by a user. Specifically, the handheld operation section 21 is provided with two types of bending operation knobs 29 that are to be used in bending operations of the bending part 26, an air/water supply button 30 for an air/water supply operation, and a suction button 31 for a suction operation. The handheld operation section 21 is further provided with a still image capturing instruction unit 32 for providing an instruction to capture a still image 39 of a portion to be observed, and a treatment tool port 33 from which a treatment tool (not illustrated) is to be inserted into a treatment tool insertion path (not illustrated) extending in and through the insertion section 20.

The universal cord 22 is a connection cord for connecting the endoscope 10 to the light source apparatus 11. The universal cord 22 includes therein a light guide 35, a signal cable 36, and a fluid tube (not illustrated) that extend in and through the insertion section 20. In addition, the universal cord 22 has an end portion provided with a connector 37a that is connected to the light source apparatus 11 and a connector 37b that branches off from the connector 37a and that is connected to the endoscope processor apparatus 12.

Connecting of the connector 37a to the light source apparatus 11 causes the light guide 35 and the fluid tube (not illustrated) to be inserted into the light source apparatus 11. Accordingly, necessary illumination light, air, and water are supplied from the light source apparatus 11 to the endoscope 10 through the light guide 35 and the fluid tube (not illustrated). As a result, the illumination light is radiated from an illumination window (not illustrated) on the distal end surface of the distal end part 27 toward a portion to be observed. An operation of pressing the above-described air/water supply button 30 causes air or water to be ejected from an air/water supply nozzle (not illustrated) on the distal end surface of the distal end part 27 toward the observation window (not illustrated) on the distal end surface.

Connecting of the connector 37b to the endoscope processor apparatus 12 causes the signal cable 36 and the endoscope processor apparatus 12 to be electrically connected to each other. Accordingly, an image signal of a portion to be observed is output from the imaging device 28 of the endoscope 10 to the endoscope processor apparatus 12, and a control signal is output from the endoscope processor apparatus 12 to the endoscope 10, through the signal cable 36.

The light source apparatus 11 supplies illumination light to the light guide 35 of the endoscope 10 via the connector 37a. As the illumination light, light in various wavelength ranges is selected in accordance with an observation purpose, for example, white light (light in a white wavelength range or light in a plurality of wavelength ranges), light in one or a plurality of specific wavelength ranges, or a combination thereof. A specific wavelength range is narrower than the white wavelength range.

A first example of the specific wavelength range is, for example, a blue range or green range in a visible range. The wavelength range in the first example includes a wavelength range of 390 nm or more and 450 nm or less or a wavelength range of 530 nm or more and 550 nm or less, and the light in the first example has a peak wavelength in the wavelength range of 390 nm or more and 450 nm or less or the wavelength range of 530 nm or more and 550 nm or less.

A second example of the specific wavelength range is, for example, a red range in the visible range. The wavelength range in the second example includes a wavelength range of 585 nm or more and 615 nm or less or a wavelength range of 610 nm or more and 730 nm or less, and the light in the second example has a peak wavelength in the wavelength range of 585 nm or more and 615 nm or less or the wavelength range of 610 nm or more and 730 nm or less.

A third example of the specific wavelength range includes a wavelength range in which a light absorption coefficient is different between oxyhemoglobin and deoxyhemoglobin, and the light in the third example has a peak wavelength in the wavelength range in which the light absorption coefficient is different between oxyhemoglobin and deoxyhemoglobin. The wavelength range in the third example includes a wavelength range of 400±10 nm, a wavelength range of 440±10 nm, a wavelength range of 470±10 nm, or a wavelength range of 600 nm or more and 750 nm or less, and the light in the third example has a peak wavelength in the wavelength range of 400±10 nm, the wavelength range of 440±10 nm, the wavelength range of 470±10 nm, or the wavelength range of 600 nm or more and 750 nm or less.

A fourth example of the specific wavelength range is a wavelength range (390 nm to 470 nm) of excitation light that is to be used in observation of fluorescence generated by a fluorescent substance in a living body (fluorescence observation) and that excites the fluorescent substance.

A fifth example of the specific wavelength range is a wavelength range of infrared light. The wavelength range in the fifth example includes a wavelength range of 790 nm or more and 820 nm or less or a wavelength range of 905 nm or more and 970 nm or less, and the light in the fifth example has a peak wavelength in the wavelength range of 790 nm or more and 820 nm or less or the wavelength range of 905 nm or more and 970 nm or less.

The endoscope processor apparatus 12 controls operations of the endoscope 10 via the connector 37b and the signal cable 36. The endoscope processor apparatus 12 generates a moving image 38, which is a time-series medical image made up of time-series frame images 38a (see FIG. 2) on the basis of image signals acquired from the imaging device 28 of the endoscope 10 via the connector 37b and the signal cable 36. The moving image 38 has a frame rate of, for example, 30 frames per second (fps).

Furthermore, when the still image capturing instruction unit 32 is operated in the handheld operation section 21 of the endoscope 10, the endoscope processor apparatus 12 acquires, while generating the moving image 38, one frame image 38a in the moving image 38 at the timing of an image capturing instruction and regards the frame image 38a as the still image 39.

The moving image 38 and the still image 39 are each a medical image acquired through imaging of the inside of a subject, that is, the inside of a living body. Furthermore, in a case where the moving image 38 and the still image 39 are each an image acquired by using light in the above-described specific wavelength range (special light), both the images are special-light images. The endoscope processor apparatus 12 outputs the generated moving image 38 and still image 39 to each of the display apparatus 13 and the medical image processing apparatus 14.

The endoscope processor apparatus 12 may generate (acquire) a special-light image having information of the above-described specific wavelength range on the basis of a normal-light image acquired by using the above-described white light. In this case, the endoscope processor apparatus 12 functions as a special-light image acquiring unit. The endoscope processor apparatus 12 acquires a signal in the specific wavelength range by performing computation based on RGB color information of red, green, and blue or CMY color information of cyan, magenta, and yellow included in the normal-light image.

The endoscope processor apparatus 12 may generate a feature-quantity image, such as a known oxygen saturation image, for example, on the basis of at least one of a normal-light image acquired by using the above-described white light or a special-light image acquired by using the above-described light in the specific wavelength range (special light). In this case, the endoscope processor apparatus 12 functions as a feature-quantity image generating unit. The moving image 38 or the still image 39, including the above-described inside-of-living-body image, normal-light image, special-light image, and feature-quantity image, is a medical image generated through imaging of a result of capturing an image of a human body or measuring the human body for the purpose of diagnosis or examination using the image.

The display apparatus 13 is connected to the endoscope processor apparatus 12 and displays the moving image 38 and the still image 39 received from the endoscope processor apparatus 12. A user performs, for example, an operation of moving the insertion section 20 forward or backward while viewing the moving image 38 displayed on the display apparatus 13. When the user finds a lesion or the like in a portion that is being observed, the user operates the still image capturing instruction unit 32 and captures a still image of the portion that is being observed, or performs diagnosis, biopsy, or the like.

The medical image processing apparatus 14 is an apparatus that automatically recognizes and automatically discriminates a lesion as a region of interest, and reports reporting information included in a medical image to a user. As the medical image processing apparatus 14, a personal computer is used, for example. As the operation unit 15, a keyboard, a mouse, and the like connected to the personal computer in a wired or wireless manner are used. As the display 16 (an example of a reporting unit), a monitor of various types, such as a liquid crystal monitor, connectable to the personal computer is used.

The medical image processing apparatus 14 and the display 16 (an example of a first display unit) function as a diagnosis support apparatus that displays the moving image 38 and reporting information on the display 16.

First Embodiment

Configuration of Medical Image Processing Apparatus

Figure 2:
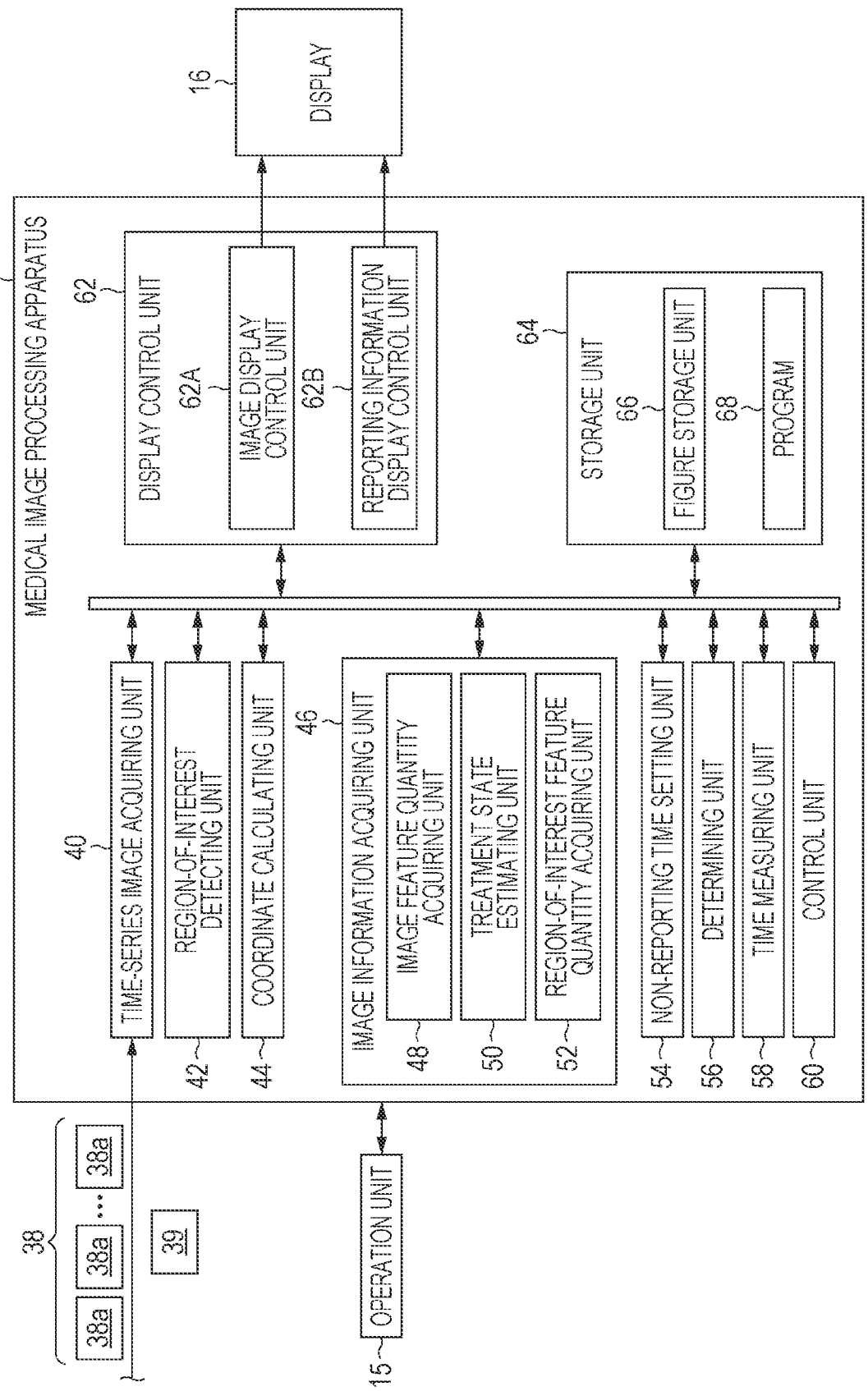
FIG. 2 is a block diagram illustrating an example of an electric configuration of the medical image processing apparatus.

FIG. 2 is a block diagram illustrating an example of an electric configuration of the medical image processing apparatus 14 according to a first embodiment. The medical image processing apparatus 14 illustrated in FIG. 2 is constituted mainly by a time-series image acquiring unit 40, a region-of-interest detecting unit 42, a coordinate calculating unit 44, an image information acquiring unit 46, a non-reporting time setting unit 54, a determining unit 56, a time measuring unit 58, a control unit 60, a display control unit 62, and a storage unit 64.

The control unit 60 centrally controls the time-series image acquiring unit 40, the region-of-interest detecting unit 42, the coordinate calculating unit 44, the image information acquiring unit 46, the non-reporting time setting unit 54, the determining unit 56, the time measuring unit 58, and the display control unit 62, and functions as part of these units, on the basis of a program (medical image processing program) 68 stored in the storage unit 64.

The storage unit 64 is a storage device, such as a hard disk device. The storage unit 64 stores a detection result of the region-of-interest detecting unit 42 and the still image 39 that has been captured, and also stores the program 68 and information or the like related to various types of control of the medical image processing apparatus 14.

The storage unit 64 includes a figure storage unit 66. The figure storage unit 66 stores a figure for reporting reporting information to a user.

The time-series image acquiring unit 40 sequentially acquires endoscopic images as an example of medical images. Here, the time-series image acquiring unit 40 acquires the moving image 38 (in this example, the moving image 38 captured by the endoscope 10) made up of the time-series frame images 38a from the endoscope processor apparatus 12 by using an image input/output interface that is connected to the endoscope processor apparatus 12 (see FIG. 1) in a wired or wireless manner and that is not illustrated. In a case where the endoscope 10 captures the above-described still image 39 while capturing the moving image 38, the time-series image acquiring unit 40 acquires the moving image 38 and the still image 39 from the endoscope processor apparatus 12.

The time-series image acquiring unit 40 may acquire the moving image 38 via an information storage medium of various types, such as a memory card or a hard disk device, instead of directly acquiring the moving image 38 from the endoscope processor apparatus 12. Alternatively, the time-series image acquiring unit 40 may acquire the moving image 38 uploaded to a server, a database, or the like on the Internet, via the Internet.

The region-of-interest detecting unit 42 is an example of a reporting information acquiring unit that acquires, from a medical image, reporting information included in the medical image, and detects a region of interest from the moving image 38 captured during observation of the inside of a subject. The region-of-interest detecting unit 42 includes a convolutional neural network (CNN) that calculates a feature quantity of each of the frame images 38a (or thinned out frame images 38a at regular intervals) of the moving image 38 and that recognizes a region of interest in the image.

Examples of a region of interest include a polyp, a cancer, a colon diverticulum, an inflammation, a scar of endoscopic mucosal resection (EMR), a scar of endoscopic submucosal dissection (ESD), a clip portion, a bleeding point, a perforation, angiodysplasia, a treatment tool, and the like.

The region-of-interest detecting unit 42 is capable of acquiring a recognition result of category classification or the like indicating a category to which a detected region of interest belongs among a plurality of categories related to a lesion, such as "neoplastic", "non-neoplastic", and "others".

The region-of-interest detecting unit 42 is not limited to a unit that detects a region of interest by using a CNN, and may be a unit that detects a region of interest by performing image processing to analyze a feature quantity, such as a color, pixel value gradient, shape, or size in an image.

The coordinate calculating unit 44 is an example of a reporting information acquiring unit and calculates coordinate information indicating a position in an image of a region of interest detected by the region-of-interest detecting unit 42. The coordinate calculating unit 44 calculates, for example, one or more pieces of coordinate information on the contour of a polygon or circle surrounding the region of interest. The coordinate calculating unit 44 may calculate, as coordinate information, the coordinates of the vertexes of a polygon or the coordinates of midpoints of the sides of a polygon, or may calculate, as coordinate information, the coordinates of points that equally divide the circumference of a circle into a plurality of segments.

The image information acquiring unit 46 is an image processing unit that acquires, from the moving image 38, image information for estimating the timing at which reporting information is not necessary or the timing at which a detection result of the region-of-interest detecting unit 42 has decreased reliability. The image information acquiring unit 46 includes an image feature quantity acquiring unit 48, a treatment state estimating unit 50, and a region-of-interest feature quantity acquiring unit 52.

The image feature quantity acquiring unit 48 acquires an image feature quantity, which is a feature quantity of each frame image 38a of the moving image 38. The treatment state estimating unit 50 analyzes each frame image 38a of the moving image 38 through image processing and estimates a treatment state of a subject. The region-of-interest feature quantity acquiring unit 52 acquires a region-of-interest feature quantity, which is a feature quantity of a region of interest detected by the region-of-interest detecting unit 42.

The non-reporting time setting unit 54 sets a non-reporting time, which will be described below. The non-reporting time is stored in, for example, the storage unit 64. The non-reporting time setting unit 54 reads out a non-reporting time from the storage unit 64 and sets the read out non-reporting time. The non-reporting time setting unit 54 may set a non-reporting time in accordance with a treatment state estimated by the treatment state estimating unit 50 or may set a value input by a user as a non-reporting time.

The determining unit 56 determines whether or not the moving image 38 satisfies a non-reporting condition. The determining unit 56 may determine whether or not the moving image 38 satisfies the non-reporting condition on the basis of image information acquired by the image information acquiring unit 46. That is, the determining unit 56 may determine whether or not the moving image 38 satisfies the non-reporting condition on the basis of at least one of an image feature quantity acquired by the image feature quantity acquiring unit 48, a treatment state estimated by the treatment state estimating unit 50, or a region-of-interest feature quantity acquired by the region-of-interest feature quantity acquiring unit 52.

The time measuring unit 58 measures a time elapsed from when the moving image 38 does not satisfy the non-reporting condition. The time measuring unit 58 may count the number of frame images 38a (the number of frames) from when the moving image 38 does not satisfy the non-reporting condition, thereby measuring the elapsed time.

The display control unit 62 controls display on the display 16. The display control unit 62 includes an image display control unit 62A and a reporting information display control unit 62B. The image display control unit 62A outputs the moving image 38 acquired by the time-series image acquiring unit 40 to the display 16 and causes the display 16 to display the moving image 38. That is, a plurality of frame images 38a are sequentially displayed on the display 16.

The reporting information display control unit 62B is an example of a reporting control unit that causes a reporting unit to report reporting information included in a medical image. The reporting information display control unit 62B performs control to bring reporting information into either a reporting state in which the reporting information is reported or a non-reporting state in which the reporting information is not reported. The reporting information display control unit 62B causes the display 16 to display, as reporting information, information about a region of interest detected by the region-of-interest detecting unit 42 in a reporting state. Here, the reporting information display control unit 62B superimposes a figure read out from the figure storage unit 66 on the position indicated by coordinate information calculated by the coordinate calculating unit 44 of the frame image 38a displayed on the display 16. Accordingly, the figure is displayed in a superimposed manner at the position of the region of interest of the moving image 38 displayed on the display 16, and the region of interest is emphasized by the figure.

The reporting information display control unit 62B brings reporting information into a non-reporting state in a case where the moving image 38 satisfies the non-reporting condition. That is, in a case where the moving image 38 satisfies the non-reporting condition, the reporting information display control unit 62B brings a figure read out from the figure storage unit 66 into a non-reporting state in which the figure is not displayed, and stops reporting of reporting information by the display 16.

Furthermore, the reporting information display control unit 62B maintains a non-reporting state from when the moving image 38 does not satisfy the non-reporting condition to when a non-reporting time set by the non-reporting time setting unit 54 elapses, and after the non-reporting time has elapsed, starts a reporting state in which the reporting information is displayed. That is, the non-reporting time is a time during which a non-reporting state is maintained after the non-reporting condition is not satisfied.

The reporting information display control unit 62B determines whether or not the time elapsed from when the moving image 38 does not satisfy the non-reporting condition exceeds the non-reporting time. If the time elapsed from the non-satisfaction does not exceed the non-reporting time, the reporting information display control unit 62B causes the reporting information to be kept in the non-reporting state.

If the time elapsed from the non-satisfaction exceeds the non-reporting time, the reporting information display control unit 62B brings the reporting information into a reporting state. Here, the reporting information display control unit 62B superimposes a figure read out from the figure storage unit 66 on the position indicated by the coordinate information calculated by the coordinate calculating unit 44 in the frame image 38a displayed on the display 16.

Assuming that the reverse of the non-reporting condition is a reporting condition, it is possible to interpret that the reporting information display control unit 62B brings reporting information into a reporting state in a case where the moving image 38 satisfies the reporting condition and brings reporting information into a non-reporting state in a case where the moving image 38 does not satisfy the reporting condition. In this case, the reporting information display control unit 62B maintains a non-reporting state from when the moving image 38 satisfies the reporting condition to when the non-reporting time elapses. The reporting information display control unit 62B starts a reporting state after the non-reporting time has elapsed from when the moving image 38 satisfies the reporting condition.

Medical Image Processing Method

Next, a medical image processing method using the medical image processing apparatus 14 will be described. The medical image processing method is performed as a result of execution of the program 68 stored in the storage unit 64 by the control unit 60.

In the present embodiment, reporting information indicates the position of a region of interest, and the medical image processing apparatus 14 displays a figure indicating the position of the region of interest on the display 16. The reporting information may indicate the presence or absence of a region of interest or may indicate a recognition result of categorization of a detected region of interest.

Figure 3:
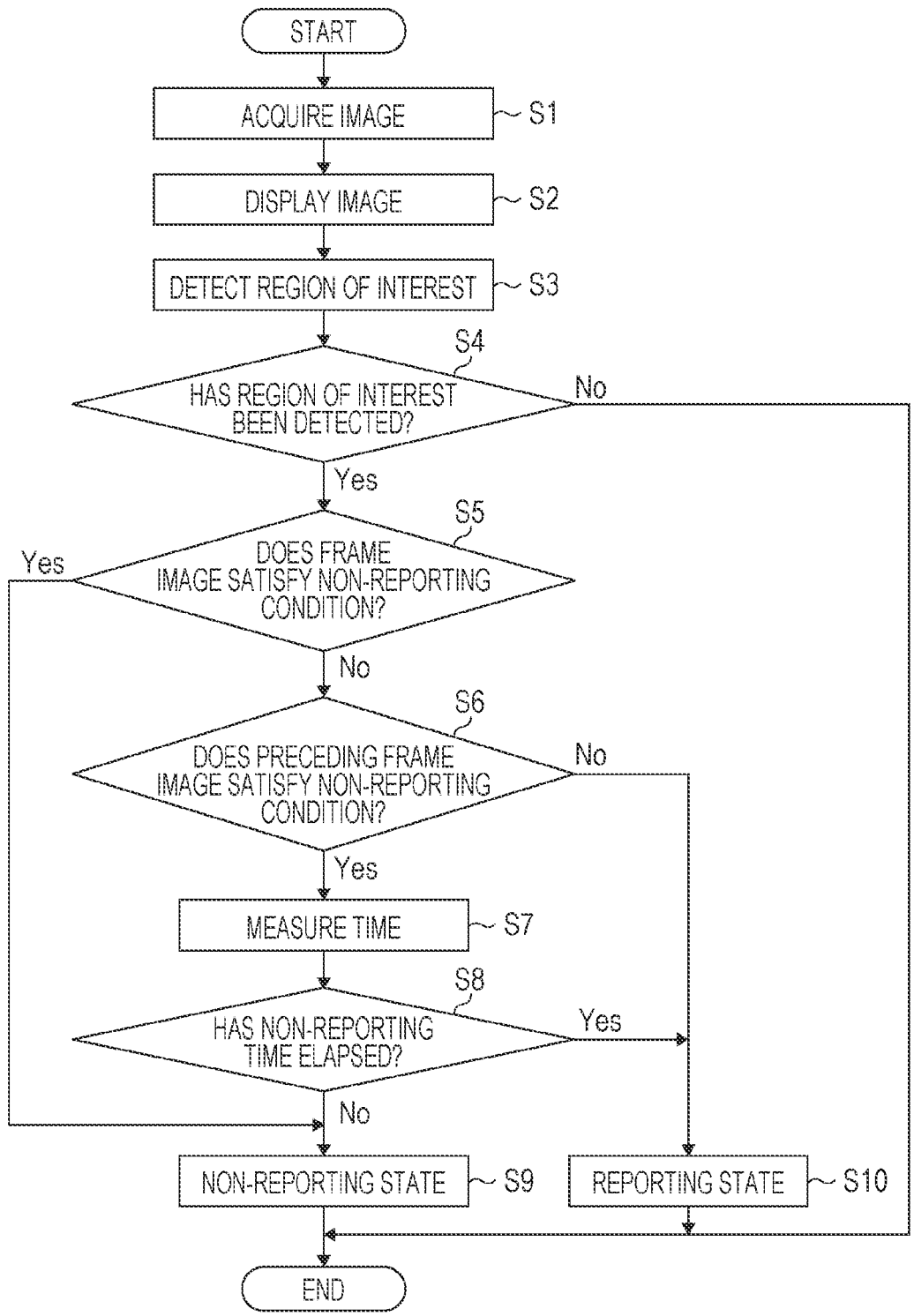
FIG. 3 is a flowchart illustrating an example of individual steps in a medical image processing method.

FIG. 3 is a flowchart illustrating an example of individual steps in the medical image processing method according to the first embodiment. The medical image processing method includes an image acquisition step (step S1), an image display step (step S2), a region-of-interest detection step (step S3), a determination step (step S5), a time measurement step (step S7), and a reporting control step (step S9 and step S10).

In step S1, the time-series image acquiring unit 40 acquires a frame image 38a of the moving image 38. In step S2, the image display control unit 62A causes the display 16 to display the frame image 38a acquired in step S1.

In step S3, the region-of-interest detecting unit 42 detects a region of interest from the frame image 38a acquired in step S1. In step S4, the control unit 60 determines whether or not a region of interest has been detected from the frame image 38a as a result of step S3.

If it is determined in step S4 that a region of interest has not been detected, the process of this flowchart ends. In this case, reporting information is absent and thus reporting information is not reported (not displayed). Thus, a figure indicating the position of a region of interest is not displayed on the display 16.

On the other hand, if it is determined in step S4 that a region of interest has been detected, the process proceeds to step S5. In step S5, the determining unit 56 determines whether or not the frame image 38a acquired in step S1 satisfies a non-reporting condition.

If it is determined in step S5 that the frame image 38a satisfies the non-reporting condition, the process proceeds to step S9. In step S9, the reporting information display control unit 62B brings reporting information into a non-reporting state (hidden state), and ends the process of this flowchart. Thus, a figure indicating the position of the region of interest is not displayed on the display 16.

On the other hand, if it is determined in step S5 that the frame image 38a does not satisfy the non-reporting condition, the process proceeds to step S6. In step S6, the determining unit 56 determines whether or not a frame image 38a preceding to the frame image 38a acquired in step S1 satisfies the non-reporting condition.

If it is determined in step S6 that the preceding frame image 38a does not satisfy the non-reporting condition, the process proceeds to step S10. In step S10, the reporting information display control unit 62B brings the reporting information into a reporting state (display state), and ends the process of this flowchart. Thus, a figure is superimposed on the position of the region of interest in the frame image 38a displayed on the display 16.

If it is determined in step S6 that the preceding frame image 38a satisfies the non-reporting condition, the process proceeds to step S7. In step S7, the time measuring unit 58 measures a time elapsed from when the moving image 38 does not satisfy the non-reporting condition.

In step S8, the reporting information display control unit 62B determines whether or not the elapsed time measured by the time measuring unit 58 exceeds a non-reporting time. Here, a predetermined time is set as the non-reporting time by the non-reporting time setting unit 54.

A time longer than 0 is set as the non-reporting time. The non-reporting time is, for example, a time of 0.5 seconds or more and 30 seconds or less. The non-reporting time is preferably a time of 1 second or more and 7 seconds or less, and more preferably a time of 2 seconds or more and 4 seconds or less.

If it is determined in step S8 that the elapsed time does not exceed the non-reporting time, the process proceeds to step S9. In step S9, as in the case of the shift from step S5, the reporting information display control unit 62B brings the reporting information into a non-reporting state, and ends the process of this flowchart. Thus, a figure indicating the position of the region of interest is not displayed on the display 16.

If it is determined in step S8 that the elapsed time exceeds the non-reporting time, the process proceeds to step S10. In step S10, as in the case of the shift from step S6, the reporting information display control unit 62B brings the reporting information into a reporting state, and ends the process of this flowchart. Thus, a figure is superimposed on the position of the region of interest in the frame image 38a displayed on the display 16.

As described above, with the medical image processing method according to the first embodiment, whether or not to report (display) reporting information of a medical image can be appropriately controlled independently of a user operation.

In this flowchart, the region-of-interest detecting unit 42 performs region-of-interest detection on the frame image 38a both in a reporting state and a non-reporting state. Alternatively, the region-of-interest detecting unit 42 may perform region-of-interest detection only in a reporting state.

Figure 4:
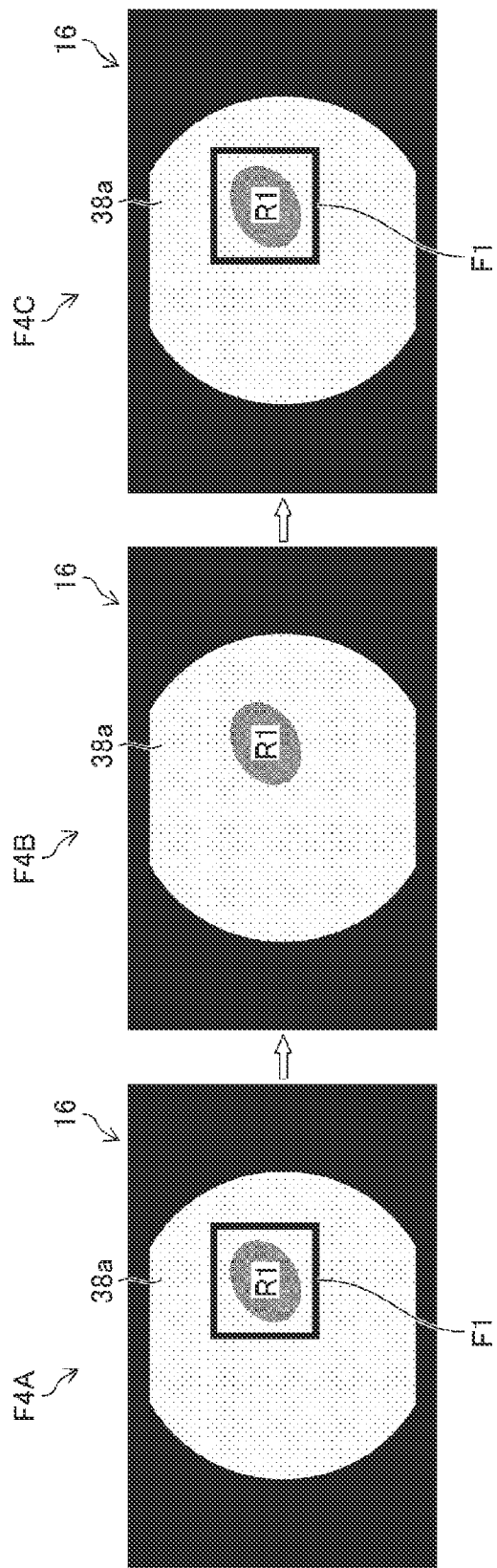
FIG. 4 is a diagram illustrating transition of display on a display.

FIG. 4 is a diagram illustrating transition of display on the display 16. Part F4A illustrated in FIG. 4 illustrates display on the display 16 at a certain time point. Part F4B illustrated in FIG. 4 illustrates display on the display 16 after a certain time has elapsed from the time point in part F4A, and part F4C illustrated in FIG. 4 illustrates display on the display 16 after a certain time has elapsed from the time point in part F4B. The frame images 38a displayed on the display 16 in parts F4A, F4B, and F4C are frame images 38a different from each other of a single moving image 38 having a constant frame rate.

Part F4A illustrates a case where the frame image 38a does not satisfy a non-reporting condition and thus reporting information is in a reporting state. In part F4A, a frame-shaped figure F1 surrounding a region of interest R1 detected in the frame image 38a is displayed on the display 16 while being superimposed on the frame image 38a. In this way, reporting of the position of the region of interest makes it possible to prevent a user from overlooking the region of interest.

Part F4B illustrates a case where the frame image 38a satisfies the non-reporting condition and thus reporting information is in a non-reporting state. In part F4B, the frame image 38a including the region of interest R1 is displayed on the display 16, but the figure F1 is not displayed because the reporting information is hidden.

When the figure F1 is displayed on the display 16, observation of the frame image 38a may be hindered depending on a situation. For example, after the user has found the region of interest R1, the figure F1 is merely an obstacle to observation. Thus, in a case where the non-reporting condition is satisfied, which may be the timing at which the reporting information is not necessary, the reporting information is hidden as illustrated in part F4B, and thus it becomes possible for the user to easily observe the medical image.

Also in a case where the figure F1 is displayed as a result of wrong detection by the region-of-interest detecting unit 42, observation of the frame image 38a is hindered. Thus, also in a case where the non-reporting condition is satisfied, which may be the timing at which the detection result of the region-of-interest detecting unit 42 has decreased reliability, the reporting information is hidden and thus it becomes possible for the user to easily observe the medical image.

Also during a time from when the frame image 38a does not satisfy the non-reporting condition to when the non-reporting time elapses, the reporting information is kept in the non-reporting state and thus the figure F1 is not displayed as in part F4B.

Part F4C illustrates a case where the reporting information has entered a reporting state again after the non-reporting time has elapsed from when the frame image 38a does not satisfy the non-reporting condition. As in part F4A, the frame-shaped figure F1 surrounding the region of interest R1 detected in the frame image 38a is displayed on the display 16 while being superimposed on the frame image 38a.

If the reporting information is kept in a non-reporting state, the reporting information is not displayed even when screening of the region of interest is restarted and the reporting information needs to be displayed, and the user may overlook the region of interest. Thus, the reporting information is brought into a reporting state in a case where the non-reporting condition is not satisfied. Accordingly, it is possible to prevent a situation from occurring where the reporting information is not displayed continuously, without a user operation for restarting display.

Here, if the reporting information is displayed immediately after the non-reporting condition is not satisfied, the reporting information may be repeatedly displayed and hidden at short intervals depending on image information of the moving image 38, which may be inconvenient to the user. Thus, a reporting state is started after the non-reporting time has elapsed from when the non-reporting condition is not satisfied. As a result of such transition from hiding to displaying, it is possible to prevent short-interval repetition of displaying and hiding.

Modification Examples of Display Manner of Reporting Region of Interest

The manner of reporting a region of interest on the display 16 is not limited to the example of surrounding the region of interest with a frame-shaped figure.

FIG. 5 to FIG. 8 are diagrams each illustrating an example of display on the display 16 in a reporting state, in which the frame image 38a including the region of interest R1 is displayed.

Figure 5:
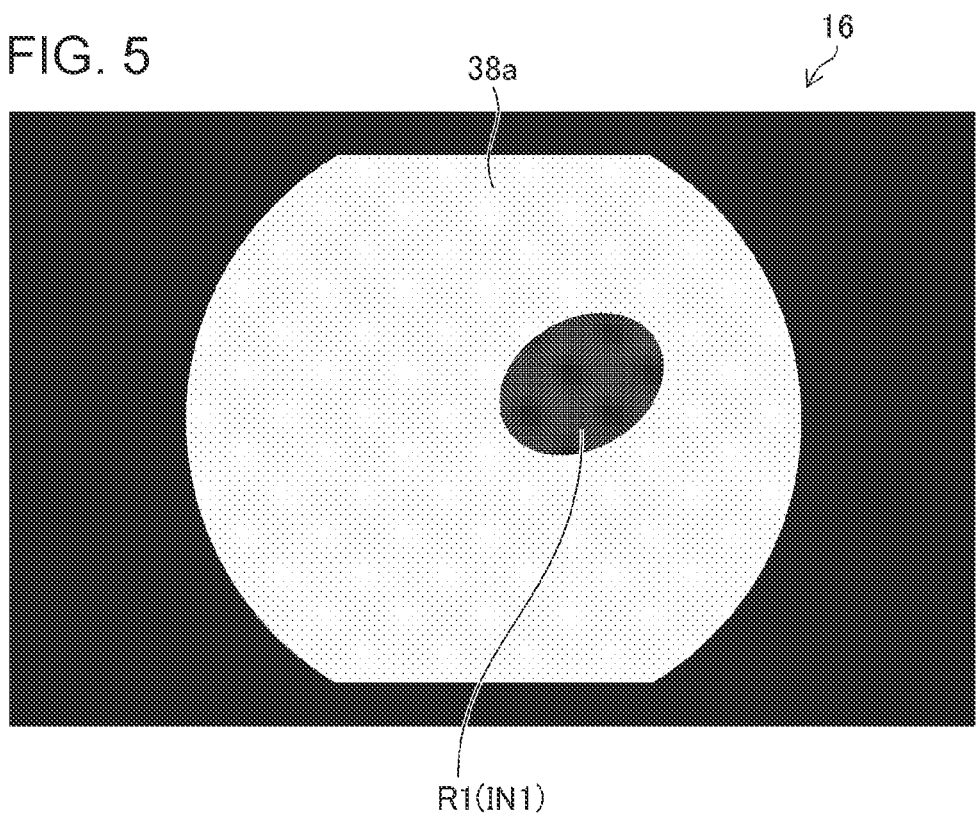
FIG. 5 is a diagram illustrating an example of display on the display in a reporting state.

In the case illustrated in FIG. 5, the reporting information display control unit 62B displays information IN1, which is the region of interest R1 that is filled in, thereby reporting the region of interest R1. The color with which the region of interest R1 is filled in is not limited as long as a user can be notified. In this way, as a result of filling in the region of interest, it is possible to report the region of interest such that the range of the region of interest can be easily recognized.

Figure 6:
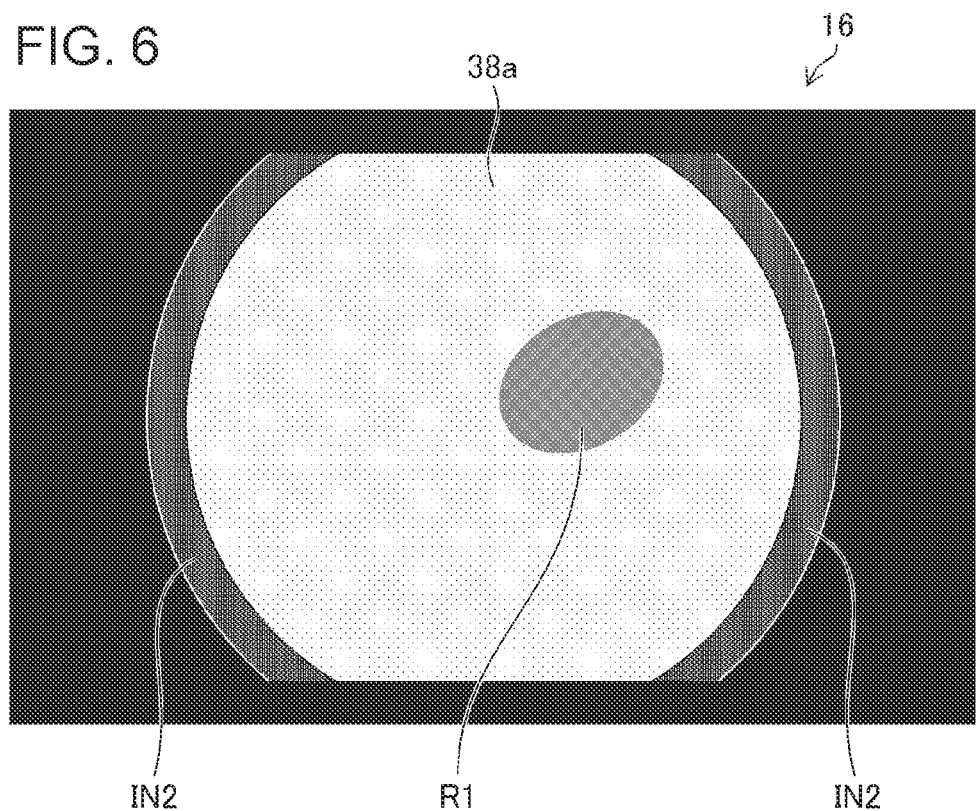
FIG. 6 is a diagram illustrating an example of display on the display in a reporting state.
Figure 7:
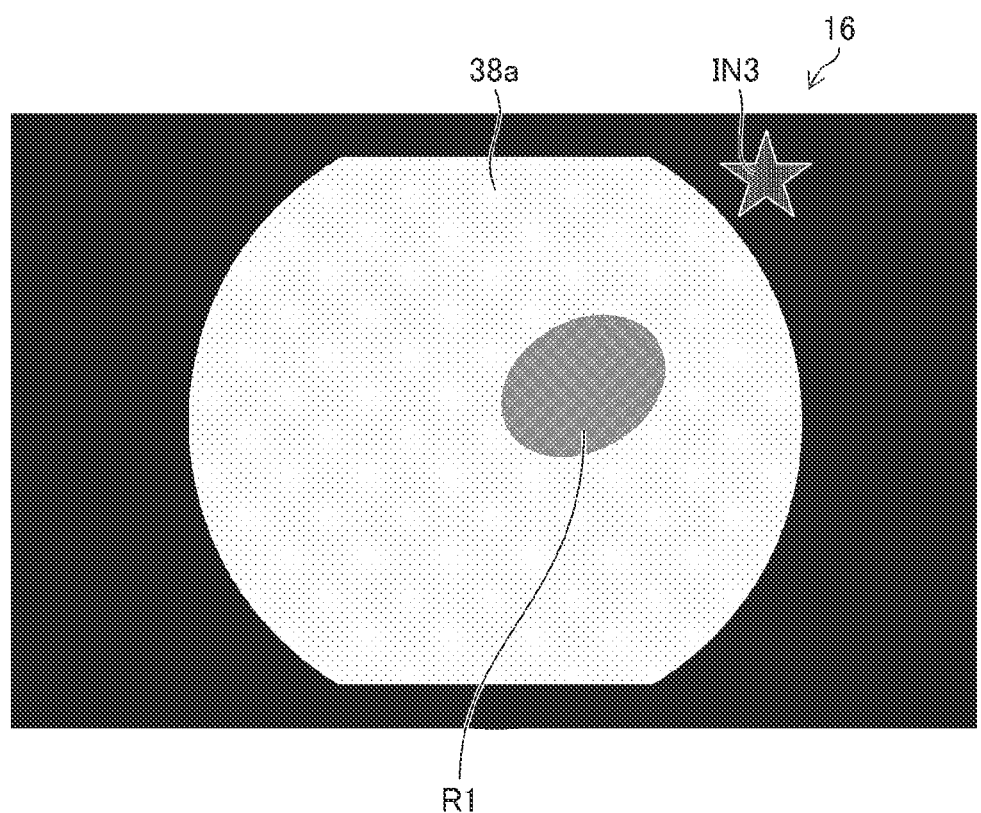
FIG. 7 is a diagram illustrating an example of display on the display in a reporting state.

FIG. 6 and FIG. 7 each illustrate an example of reporting whether or not a region of interest has been detected regardless of the position of the region of interest in an image.

In the case illustrated in FIG. 6, the reporting information display control unit 62B displays information IN2, which is a colored periphery of the frame image 38a, thereby reporting that the region of interest R1 has been detected. In this way, as a result of using a colored periphery of a medical image for reporting, it is possible to perform reporting with a reduced movement of the line of sight of a user and without superimposing a figure that hinders observation on the medical image.

In the example illustrated in FIG. 7, the reporting information display control unit 62B displays information IN3, which is a star-shaped figure, at an upper-right position outside the frame image 38a, thereby reporting that the region of interest R1 has been detected. The shape and position of the figure are not limited to those in this example. In this way, as a result of displaying a specific figure at a specific position outside a medical image, it is possible to perform reporting with a reduced movement of the line of sight of a user and without superimposing a figure that hinders observation on the medical image. In addition, such reporting has an influence on a small range in a display screen, which is advantageous in that reporting does not disturb the user.

Figure 8:
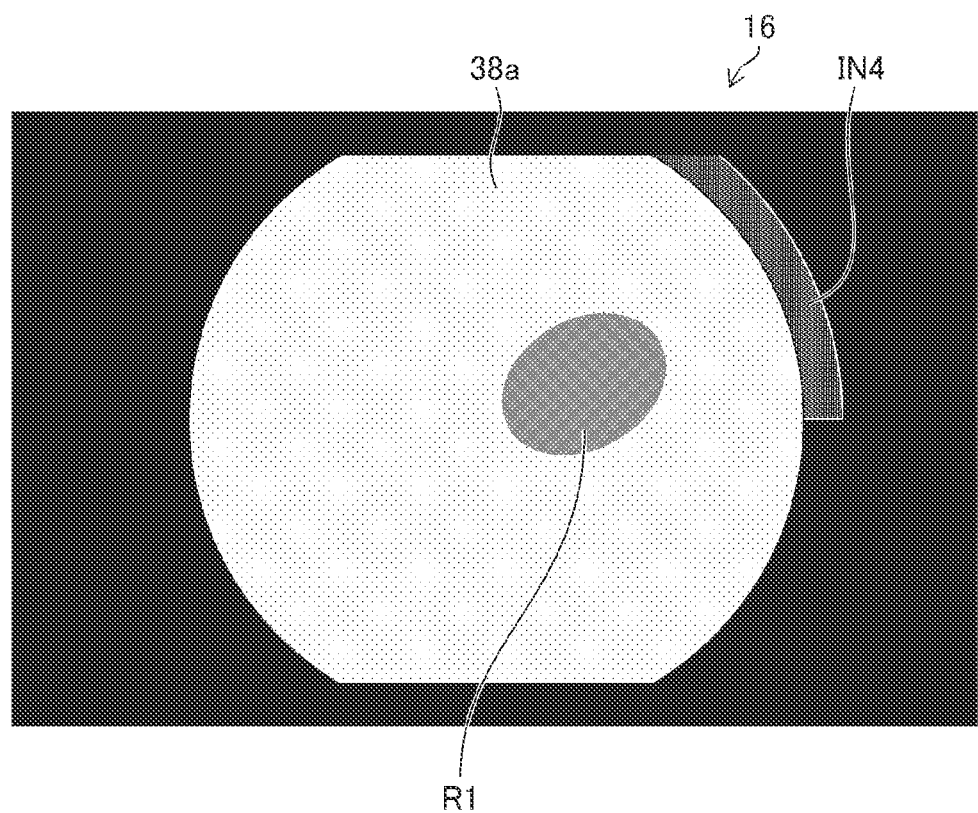
FIG. 8 is a diagram illustrating an example of display on the display in a reporting state.

In the case illustrated in FIG. 8, the reporting information display control unit 62B displays information IN4, which is a colored region (here, the upper right) close to the region of interest in a periphery of the frame image 38a, thereby roughly reporting the position of the region of interest R1. In this way, as a result of reporting a region close to the region of interest in the periphery of a medical image by using a color, it is possible to perform reporting so that the position of the detection target can be roughly grasped, without superimposing a figure that hinders observation on the medical image.

Display of Other Information

Figure 9:
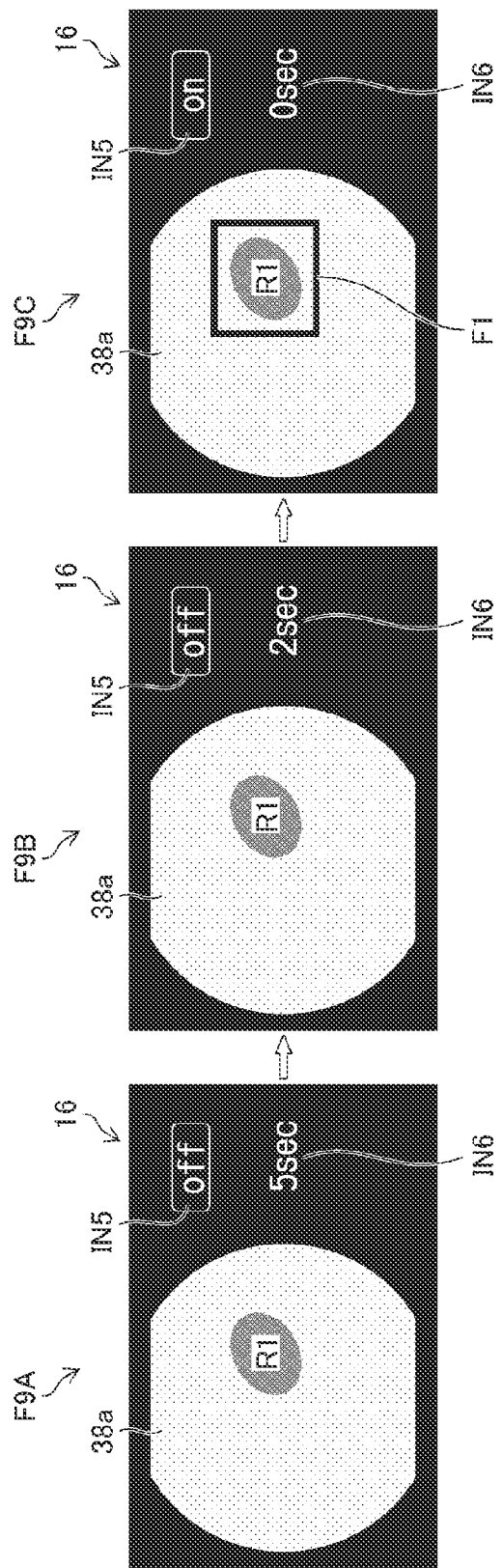
FIG. 9 is a diagram illustrating transition of display on the display.

FIG. 9 is a diagram illustrating transition of display on the display 16. Part F9A illustrated in FIG. 9 illustrates display on the display 16 at a certain time point. Part F9B illustrated in FIG. 9 illustrates display on the display 16 after 3 seconds have elapsed from the time point in part F9A. Part F9C illustrated in FIG. 9 illustrates display on the display 16 after 2 seconds have elapsed from the time point in part F9B. The frame images 38a displayed on the display 16 in parts F9A, F9B, and F9C are frame images 38a different from each other in a single moving image 38 having a constant frame rate.

In parts F9A, F9B, and F9C, information IN5 indicating a reporting state or a non-reporting state (an example of information indicating that reporting information is in a non-reporting state), and information IN6 indicating a remaining time during which reporting information is to be kept in a non-reporting state, that is, a difference between a non-reporting time and an elapsed time (an example of information about a time elapsed from when a medical image does not satisfy the non-reporting condition) are displayed in a display region (an example of a third display unit) different from a display region of the frame image 38a (an example of a first display unit) on the display 16.

Parts F9A and F9B each illustrate a case of a non-reporting state. In parts F9A and F9B, the frame image 38a including the region of interest R1 is displayed on the display 16, but the reporting information display control unit 62B does not report the region of interest R1.

In part F9A, the reporting information display control unit 62B displays "off" indicating that reporting information is in a non-reporting state as the information IN5, and displays "5 sec" indicating that the remaining time is 5 seconds as the information IN6. In part F9B, the reporting information display control unit 62B displays "off" indicating that reporting information is in a non-reporting state as the information IN5, and displays "2 sec" indicating that the remaining time is 2 seconds as the information IN6.

Part F9C illustrates a case where a reporting state has started after the non-reporting time has elapsed. In part F9C, the frame image 38a including the region of interest R1 is displayed on the display 16, and the reporting information display control unit 62B superimposes the frame-shaped figure F1 surrounding the region of interest R1 on the frame image 38a. In part F9C, the reporting information display control unit 62B displays "on" indicating that reporting information is in a reporting state as the information IN5, and displays "0 sec" indicating that the non-reporting time has elapsed as the information IN6. The reporting information display control unit 62B may hide the information IN6 during a reporting state.

Figure 10:
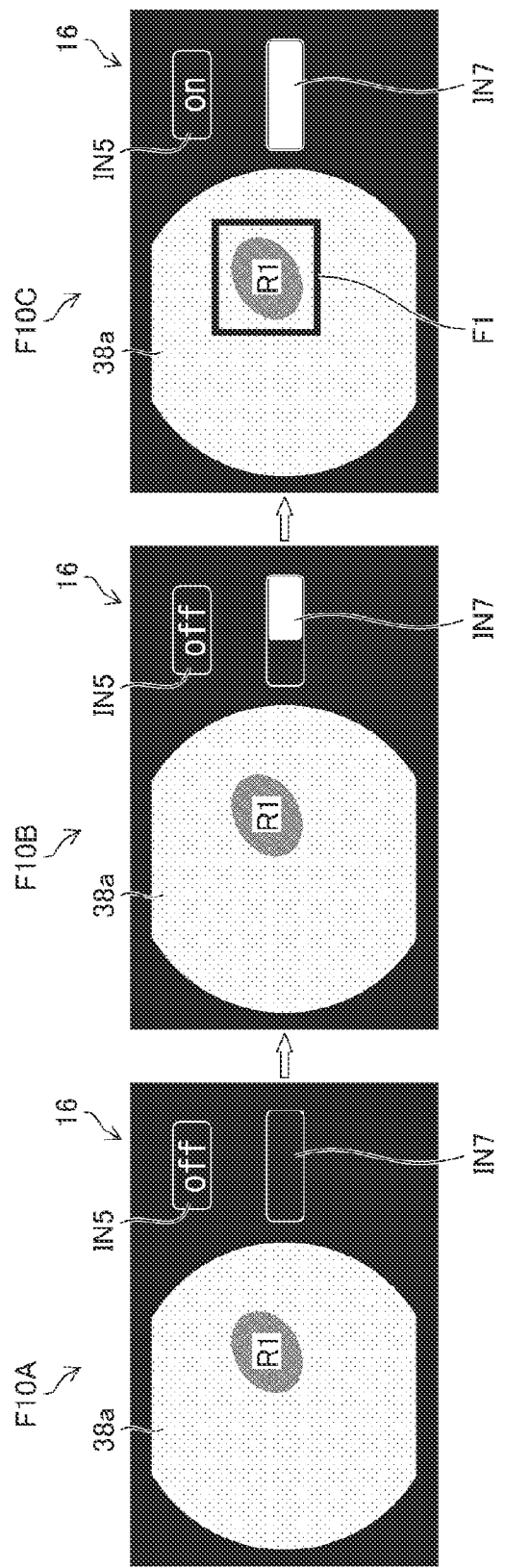
FIG. 10 is a diagram illustrating transition of display on the display.
Figure 11:
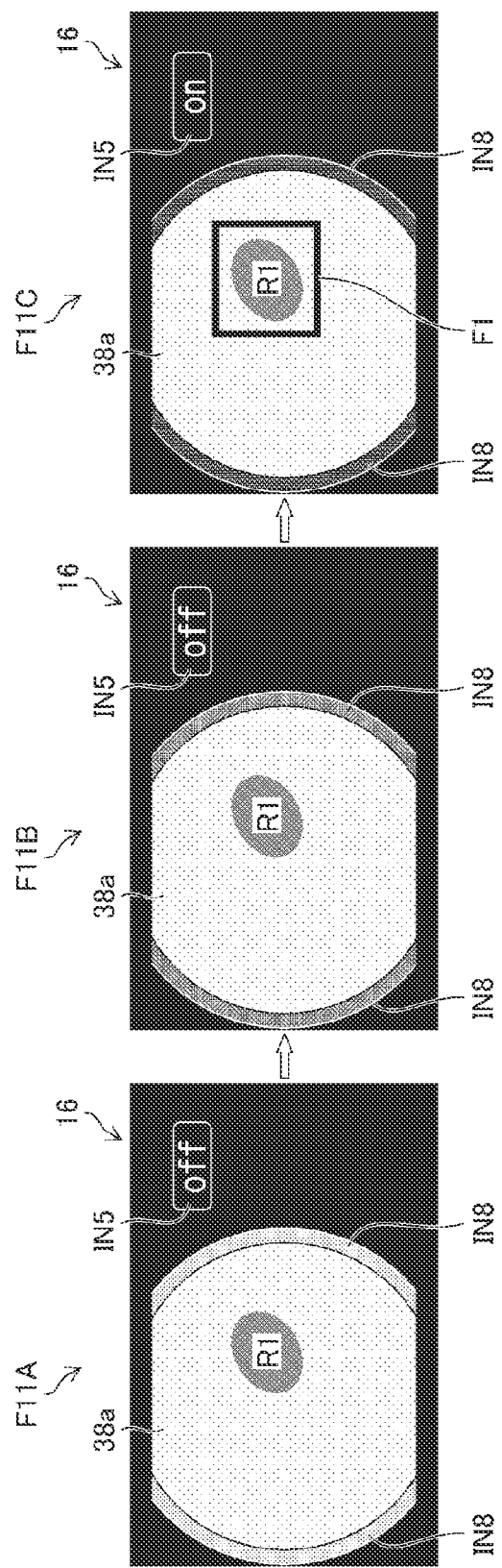
FIG. 11 is a diagram illustrating transition of display on the display.

FIG. 10 and FIG. 11 are each a diagram illustrating transition of display on the display 16. The transition timings between parts F10A, F10B, and F10C illustrated in FIG. 10 and the transition timings between parts F11A, F11B, and F11C illustrated in FIG. 11 are similar to the transition timings between parts F9A, F9B, and F9C illustrated in FIG. 9, respectively. That is, the frame images 38a displayed in parts F10A, F10B, and F10C and the frame images 38a displayed in parts F11A, F11B, and F11C are similar to the frame images displayed in parts F9A, F9B, and F9C, respectively.

In parts F10A, F10B, and F10C, information IN5 indicating a reporting state or a non-reporting state, and information IN7 indicating a remaining time during which reporting information is to be kept in a non-reporting state (an example of information about a time elapsed from when a medical image does not satisfy the non-reporting condition) are displayed in a display region different from the display region of the frame image 38a on the display 16.

The information IN7 represents the remaining time of a non-reporting state by using a bar (progress bar) and is set such that the length of a filled-in portion of the bar is correlated with an elapsed time.

Parts F10A and F10B each illustrate a case of a non-reporting state. In parts F10A and F10B, the frame image 38a including the region of interest R1 is displayed on the display 16, but the reporting information display control unit 62B does not report the region of interest R1. In part F10A, the reporting information display control unit 62B displays "off" indicating that reporting information is in a non-reporting state as the information IN5, and displays a bar whose portion corresponding to a remaining time of 5 seconds is filed in as the information IN7. In part F10B, the reporting information display control unit 62B displays "off" indicating that reporting information is in a non-reporting state as the information IN5, and displays a bar whose portion corresponding to a remaining time of 2 seconds is filed in as the information IN7.

Part F10C illustrates a case where a reporting state has started after the non-reporting time has elapsed. In part F10C, the frame image 38a including the region of interest R1 is displayed on the display 16, and the reporting information display control unit 62B superimposes the frame-shaped figure F1 surrounding the region of interest R1 on the frame image 38a. In part F10C, the reporting information display control unit 62B displays "on" indicating that reporting information is in a reporting state as the information IN5, and displays a bar whose portion corresponding to a remaining time of 0 seconds is filled in, that is, a bar that is not filled in, as the information IN7. The reporting information display control unit 62B may hide the information IN7 during a reporting state.

In this way, as a result of displaying a bar in which the length of a filled-in portion is correlated with an elapsed time, the user is able to graphically interpret the remaining time.

In parts F11A, F11B, and F11C, information IN5 indicating a reporting state or a non-reporting state, and information IN8 indicating a remaining time during which reporting information is to be kept in a non-reporting state (an example of information about a time elapsed from when a medical image does not satisfy the non-reporting condition) are displayed in a display region different from the display region of the frame image 38a on the display 16.

The information IN8 represents a remaining time by using color information in part of a display region. The density of the color increases as the remaining time decreases.

Parts F11A and F11B each illustrate a case of a non-reporting state. In parts F11A and F11B, the frame image 38a including the region of interest R1 is displayed on the display 16, but the reporting information display control unit 62B does not report the region of interest R1. In part F11A, the reporting information display control unit 62B displays "off" indicating that reporting information is in a non-reporting state as the information IN5, and displays a color with a density corresponding to a remaining time of 5 seconds as the information IN8. In part F11B, the reporting information display control unit 62B displays "off" indicating that reporting information is in a non-reporting state as the information IN5, and displays a color with a density corresponding to a remaining time of 2 seconds as the information IN8.

Part F11C illustrates a case where a reporting state has started after the non-reporting time has elapsed. In part F11C, the frame image 38a including the region of interest R1 is displayed on the display 16, and the reporting information display control unit 62B superimposes the frame-shaped figure F1 surrounding the region of interest R1 on the frame image 38a. In part F11C, the reporting information display control unit 62B displays "on" indicating that reporting information is in a reporting state as the information IN5, and displays a color with a density corresponding to a remaining time of 0 seconds as the information IN8.

Here, the density of the color of the information IN8 in part F11B is higher than the density of the color of the information IN8 in part F11A, and the density of the color of the information IN8 in part F11C is higher than the density of the color of the information IN8 in part F11B. The density of the color may be increased as the remaining time decreases.

In this way, as a result of representing a remaining time by using the density of the color of a periphery of a display region of a medical image, a user is able to grasp the remaining time without carefully viewing a specific region, which is advantageous in that observation is not hindered.

Figure 12:
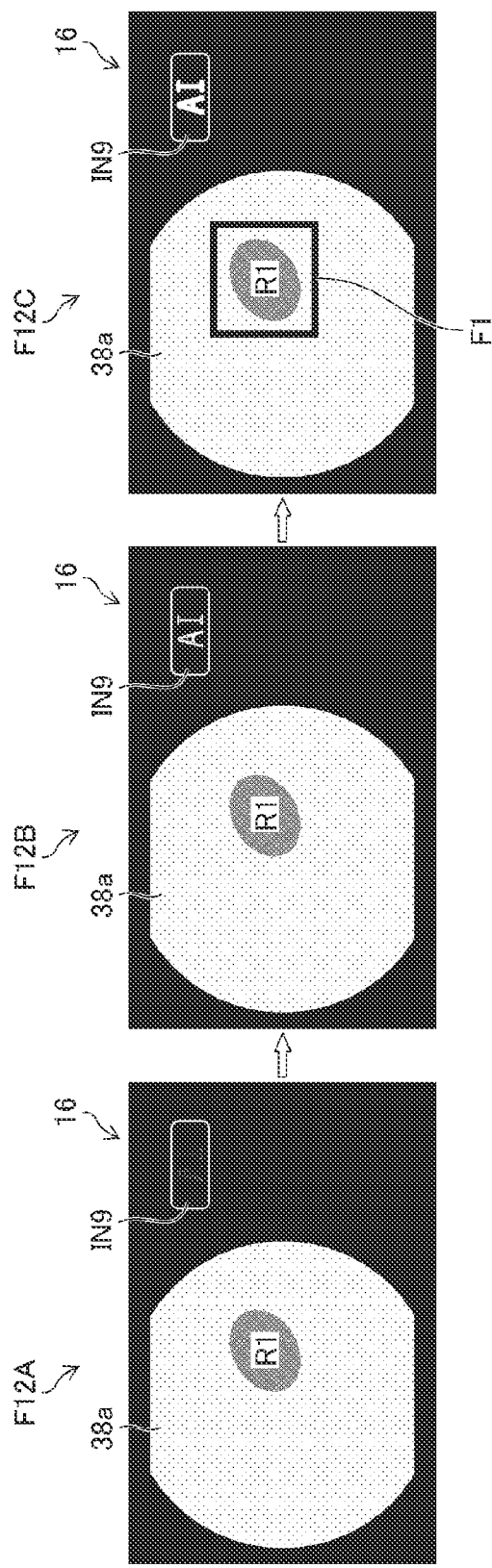
FIG. 12 is a diagram illustrating transition of display on the display.

FIG. 12 is a diagram illustrating transition of display on the display 16. Part F12A illustrated in FIG. 12 illustrates display on the display 16 at a certain time point. Part F12B illustrated in FIG. 12 illustrates display on the display 16 after a certain time has elapsed from the time point in part F12A. Part F12C illustrated in FIG. 12 illustrates display on the display 16 after a certain time has elapsed from the time point in part F12B. The frame images 38a displayed on the display 16 in parts F12A, F12B, and F12C are frame images 38a different from each other in a single moving image 38 having a constant frame rate.

In parts F12A, F12B, and F12C, information IN9 representing information indicating a reporting state or a non-reporting state and information indicating a remaining time during which reporting information is to be kept in a non-reporting state is displayed in a display region different from the display region of the frame image 38a on the display 16.

The information IN9 in which the characters "AI" are grayed out indicates a non-reporting state in which the non-reporting condition is satisfied. The information IN9 in which the characters "AI" are red with a certain density indicates a reporting state. Furthermore, in a non-reporting state from when the non-reporting condition is not satisfied to when the non-reporting time elapses, the density of red continuously changes in accordance with a remaining time.

Part F12A illustrates a case of a non-reporting state in which the non-reporting condition is satisfied. In part F12A, the frame image 38a including the region of interest R1 is displayed on the display 16, but the reporting information display control unit 62B does not report the region of interest R1. The reporting information display control unit 62B displays the grayed out characters of "AI" as the information IN9. This indicates that reporting of detection of a region of interest by artificial intelligence (AI) does not function.

Part F12B illustrates a case of a non-reporting state from when the non-reporting condition is not satisfied to when the non-reporting time elapses. In part F12B, the frame image 38a including the region of interest R1 is displayed on the display 16, but the reporting information display control unit 62B does not report the region of interest R1. The reporting information display control unit 62B displays the red characters of "AI" having a density corresponding to a remaining time as the information IN9.

Part F12C illustrates a case of a reporting state. In part F12C, the frame image 38a including the region of interest R1 is displayed on the display 16, and the reporting information display control unit 62B superimposes the frame-shaped figure F1 surrounding the region of interest R1 on the frame image 38a. The reporting information display control unit 62B displays the red characters of "AI" having a certain density corresponding to the reporting state as the information IN9. This indicates that reporting of detection of a region of interest functions.

Here, the density of red of the information IN9 in part F12C is higher than the density of red of the information IN9 in part F12B. The color of the information IN9 in a non-reporting state in which the non-reporting condition is satisfied, and the color and density of the information IN9 in a reporting state are not limited to this example.

In this way, representing together information indicating a reporting state or a non-reporting state and information indicating a remaining time is advantageous in that screen display is simplified. In addition, a difference in the color of characters between a reporting state and a non-reporting state enables a user to easily identify the reporting state and the non-reporting state. Furthermore, continuous change in the density of the color of the characters according to a remaining time enables a user to grasp a remaining time. In the case of a non-reporting state, the characters may be hidden instead of being grayed out. The remaining time may be represented by light and shade of a figure, such as an icon, instead of characters.

Details of Non-Reporting Condition

Case of Determining Image Feature Quantity

The non-reporting condition determined by the determining unit 56 is, for example, a condition of determining an image feature quantity of a medical image. The image feature quantity includes at least one of a luminance of the medical image, color information of the medical image, a temporal change in the medical image, or frequency information of the medical image.

For example, a time during which a user is observing a region of interest after finding the region of interest from the moving image 38 may be a time during which reporting information is not necessary. Typically, during observation of the region of interest, a temporal change in the moving image 38 is relatively small.

Thus, the image feature quantity acquiring unit 48 detects a temporal change in the plurality of frame images 38a of the moving image 38 as an image feature quantity. The determining unit 56 compares the detected temporal change with a temporal change set as a non-reporting condition. As a result, if it is determined that the detected temporal change is smaller, the reporting information display control unit 62B determines that the user is observing a region of interest after finding it and brings the reporting information into a non-reporting state.

Also, a time during which the endoscope system 9 is supplying or sucking water may be a time during which reporting information is not necessary. Typically, while water is being supplied or sucked, the amount of yellow components and high-frequency components of the frame image 38a is large.

Thus, the image feature quantity acquiring unit 48 detects color components of the frame image 38a as an image feature quantity. The determining unit 56 compares detected yellow components with yellow components set as a non-reporting condition. As a result, if it is determined that the amount of the detected yellow components is larger, the reporting information display control unit 62B determines that the endoscope system 9 is supplying or sucking water and brings the reporting information into a non-reporting state.

Likewise, the image feature quantity acquiring unit 48 detects frequency components of the frame image 38a as an image feature quantity. The determining unit 56 compares detected high-frequency components with high-frequency components set as a non-reporting condition. As a result, if it is determined that the amount of the detected high-frequency components is larger, the reporting information display control unit 62B determines that the endoscope system 9 is supplying or sucking water and brings the reporting information into a non-reporting state.

A case where the frame image 38a has a too high or low luminance or a case where the frame image 38a is extremely blurred may be a time at which a detection result of the region-of-interest detecting unit 42 has decreased reliability.

Thus, the image feature quantity acquiring unit 48 detects a luminance of the frame image 38a as an image feature quantity. The determining unit 56 compares the detected luminance with a luminance range set as a non-reporting condition. As a result, if it is determined that the detected luminance is not included in the set luminance range, the reporting information display control unit 62B determines that the accuracy of a detection result of the region-of-interest detecting unit 42 degrades and brings the reporting information into a non-reporting state.

Likewise, the image feature quantity acquiring unit 48 detects a blur of the frame image 38a as an image feature quantity. The determining unit 56 compares the detected blur with a blur set as a non-reporting condition. As a result, if it is determined that the detected blur is larger, the reporting information display control unit 62B determines that the accuracy of a detection result of the region-of-interest detecting unit 42 degrades and brings the reporting information into a non-reporting state.

In this way, the non-reporting condition is set to the image feature quantity at the timing at which reporting information is not necessary or the timing at which a region-of-interest detection result has decreased reliability, and the determining unit 56 compares the set image feature quantity with an image feature quantity acquired by the image feature quantity acquiring unit 48. Accordingly, the reporting information can be brought into a non-reporting state at an appropriate timing.

In a case where the non-reporting condition of determining an image feature quantity is not satisfied, reporting information should not immediately be brought into a reporting state. For example, in a case where a temporal change in the frame images 38a is small, there is often a situation in which a temporal change temporarily becomes large due to a body movement and then the amount of temporal change quickly becomes small. Such a timing at which a temporal change is temporarily large is not a timing at which screening restarts, and it is not necessary to display reporting information. If displaying and hiding are repeated at short intervals, the user may feel uncomfortable. Thus, after the non-reporting condition is not satisfied, the non-reporting state is maintained until the non-reporting time elapses, and a reporting state is started after the non-reporting time has elapsed. Accordingly, such a problem can be avoided.

Case of Determining Treatment State

The non-reporting condition may be a condition of determining a treatment state of a subject in a medical image. A time during which a user is giving treatment to a subject may be a time during which reporting information is not necessary. The treatment state may correspond to a case where a treatment tool is seen in the frame image 38a, a case where bleeding is seen in the frame image 38a, a case where the endoscope system 9 is set to an enlargement mode in which imaging is performed with enlargement at a predetermined magnification, or the like.

For example, the treatment state estimating unit 50 detects a treatment tool from the frame image 38a. The determining unit 56 compares the detected treatment tool with a treatment tool set as a non-reporting condition, such as biopsy forceps or a snare. If it is determined that the detected treatment state satisfies the non-reporting condition, the reporting information display control unit 62B determines that a user is giving treatment and brings the reporting information into a non-reporting state.

In a case where a treatment tool is detected from the frame image 38a, it may be determined that the user is giving treatment and the reporting information may be brought into a non-reporting state regardless of the type of the treatment tool. In this case, the determining unit 56 does not need to determine whether or not the non-reporting condition is satisfied, or may set all treatment tools as a non-reporting condition to make a determination.

The treatment state estimating unit 50 detects a bleeding volume from the frame image 38a. The determining unit 56 compares the detected bleeding volume with a bleeding volume set as a non-reporting condition. If it is determined that the detected bleeding volume satisfies the non-reporting condition, the reporting information display control unit 62B determines that a user is giving treatment and brings the reporting information into a non-reporting state.

The treatment state estimating unit 50 detects a mode to which the endoscope system 9 is set. The determining unit 56 compares the detected mode with the enlargement mode set as a non-reporting condition. If it is determined that the detected mode satisfies the non-reporting condition, the reporting information display control unit 62B determines that a user is giving treatment and brings the reporting information into a non-reporting state.

The treatment state estimating unit 50 detects a coloring agent applied into a subject. The determining unit 56 compares the detected coloring agent with a coloring agent set as a non-reporting condition. If it is determined that the detected coloring agent satisfies the non-reporting condition, the reporting information display control unit 62B determines that a user is making a diagnosis and brings the reporting information into a non-reporting state.

In a case where a coloring agent is detected, it may be determined that a user is giving treatment and the reporting information may be brought into a non-reporting state regardless of the type of the coloring agent. In this case, the determining unit 56 does not need to determine whether or not the non-reporting condition is satisfied, or may set all coloring agents as the non-reporting condition to make a determination.

In this way, the non-reporting condition is set to the treatment state at the timing at which reporting information is not necessary, and the determining unit 56 compares the set treatment state with a treatment state acquired by the treatment state estimating unit 50. Accordingly, the reporting information can be brought into a non-reporting state at an appropriate timing.

In a case where the non-reporting condition of determining a treatment state is not satisfied, display of reporting information should not immediately be restarted. For example, in a case where biopsy forceps are included in the frame image 38a in a non-reporting state, there is often a situation in which the forceps are covered with a mucous membrane or residual liquid and are not seen temporarily, and then the forceps are seen again. Immediately restarting display at such a timing at which forceps are not seen temporarily is not preferable for a reason similar to that in the case of determining an image feature quantity. Thus, after the non-reporting condition is not satisfied, the non-reporting state is maintained until the non-reporting time elapses, and a reporting state is started after the non-reporting time has elapsed. Accordingly, such a problem can be avoided.

The non-reporting time may be changed in accordance with a treatment state. For example, in a case where biopsy forceps are included in the frame image 38a, it can be determined, when the biopsy forceps are not seen at a forceps port any more, that biopsy treatment has finished. Thus, the non-reporting time setting unit 54 may set a relatively short time as the non-reporting time after the biopsy forceps are not seen at the forceps port any more.

On the other hand, in the case of treatment such as endoscopic mucosal resection (EMR), a series of steps including a local injection, resection with a snare, and hemostasis with a clip are performed. For example, it is not possible to detect a treatment tool from the frame image 38a after the local injection until the snare is inserted through the forceps port. During this time, a treatment operation is being performed and thus reporting information should not be redisplayed. Thus, in response to detection of a local injection from the frame image 38a, the non-reporting time setting unit 54 sets a relatively long time as the non-reporting time after the local injection is not detected any more, and thus it is possible to avoid redisplay of reporting information during the series of operations.

Case of Determining Region-of-Interest Feature Quantity

The non-reporting condition may be a condition of determining a region-of-interest feature quantity of a medical image. The region-of-interest feature quantity includes at least one of the area of a region of interest, the position of the region of interest in a medical image, or a temporal change in the region of interest.

Typically, during observation of a region of interest, the ratio of the area of the region of interest to the frame image 38a is high, the position of the region of interest is at a center portion of the frame image 38a, and a temporal change in the region of interest is small.

Thus, the region-of-interest feature quantity acquiring unit 52 detects, as a region-of-interest feature quantity, the area of the region of interest in the frame image 38a. The determining unit 56 compares the detected area with an area set as a non-reporting condition. As a result, if it is determined that the detected area is larger, the reporting information display control unit 62B determines that a user is observing the region of interest after finding it and brings the reporting information into a non-reporting state.

The region-of-interest feature quantity acquiring unit 52 detects, as a region-of-interest feature quantity, the position of the region of interest in the frame image 38a. The determining unit 56 compares the detected position with a position set as a non-reporting condition. As a result, if it is determined that the detected position of the region of interest is closer to the center portion than the position set as the non-reporting condition, the reporting information display control unit 62B determines that a user is observing the region of interest after finding it and brings the reporting information into a non-reporting state.

Likewise, the region-of-interest feature quantity acquiring unit 52 detects, as a region-of-interest feature quantity, a temporal change in the region of interest in the moving image 38. The determining unit 56 compares the detected temporal change with a temporal change set as a non-reporting condition. As a result, if it is determined that the detected temporal change is smaller, the reporting information display control unit 62B determines that a user is observing the region of interest after finding it and brings the reporting information into a non-reporting state.

In this way, the non-reporting condition is set to the region-of-interest feature quantity at the timing at which reporting information is not necessary, and the determining unit 56 compares the set region-of-interest feature quantity with a region-of-interest feature quantity acquired by the region-of-interest feature quantity acquiring unit 52. Accordingly, the reporting information can be brought into a non-reporting state at an appropriate timing.

As in the foregoing cases, in a case where the non-reporting condition of determining a region-of-interest feature quantity is not satisfied, display of reporting information should not immediately be restarted. For example, there may be a case where a region of interest actually having a large area is temporarily and partially covered with residual liquid or the like and is determined to have a small area, a case where a region of interest located at a center portion of the frame image 38a temporarily moves to an edge portion of the frame image 38a due to a body movement, or the like. Thus, after the non-reporting condition is not satisfied, the non-reporting state is maintained until the non-reporting time elapses, and a reporting state is started after the non-reporting time has elapsed. Accordingly, such a problem can be avoided.

Second Embodiment

Configuration of Medical Image Processing Apparatus

A description has been given above of an example in which the single display 16 is connected to the medical image processing apparatus 14. Alternatively, the medical image processing apparatus 14 may be connected to a plurality of display devices.

Figure 13:
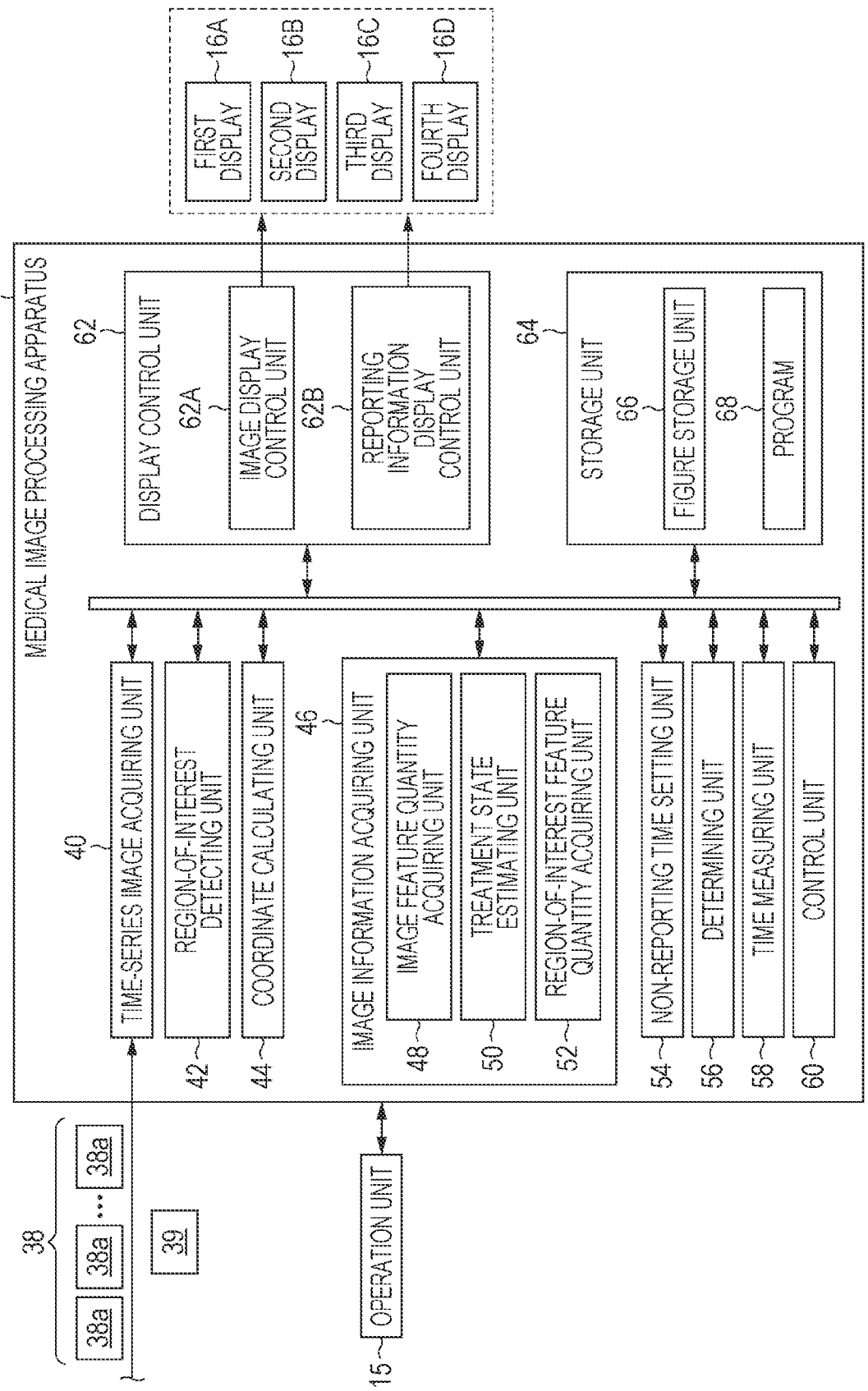
FIG. 13 is a block diagram illustrating an electric configuration of a medical image processing apparatus.

FIG. 13 is a block diagram illustrating an electric configuration of a medical image processing apparatus 14 according to a second embodiment. The medical image processing apparatus 14 is similar to the block diagram illustrated in FIG. 2. The display control unit 62 is connected to a first display 16A, a second display 16B, a third display 16C, and a fourth display 16D, and controls display on the individual displays.

The first display 16A, the second display 16B, the third display 16C, and the fourth display 16D are included in the endoscope system 9, for example. The first display 16A, the second display 16B, the third display 16C, and the fourth display 16D are display devices, such as liquid crystal monitors, different from each other. Here, the display control unit 62 is connected to four display devices, but the number of display devices may be determined as necessary. The first display 16A, the second display 16B, the third display 16C, and the fourth display 16D may be regions different from each other in a screen of a single display device.

Figure 14:
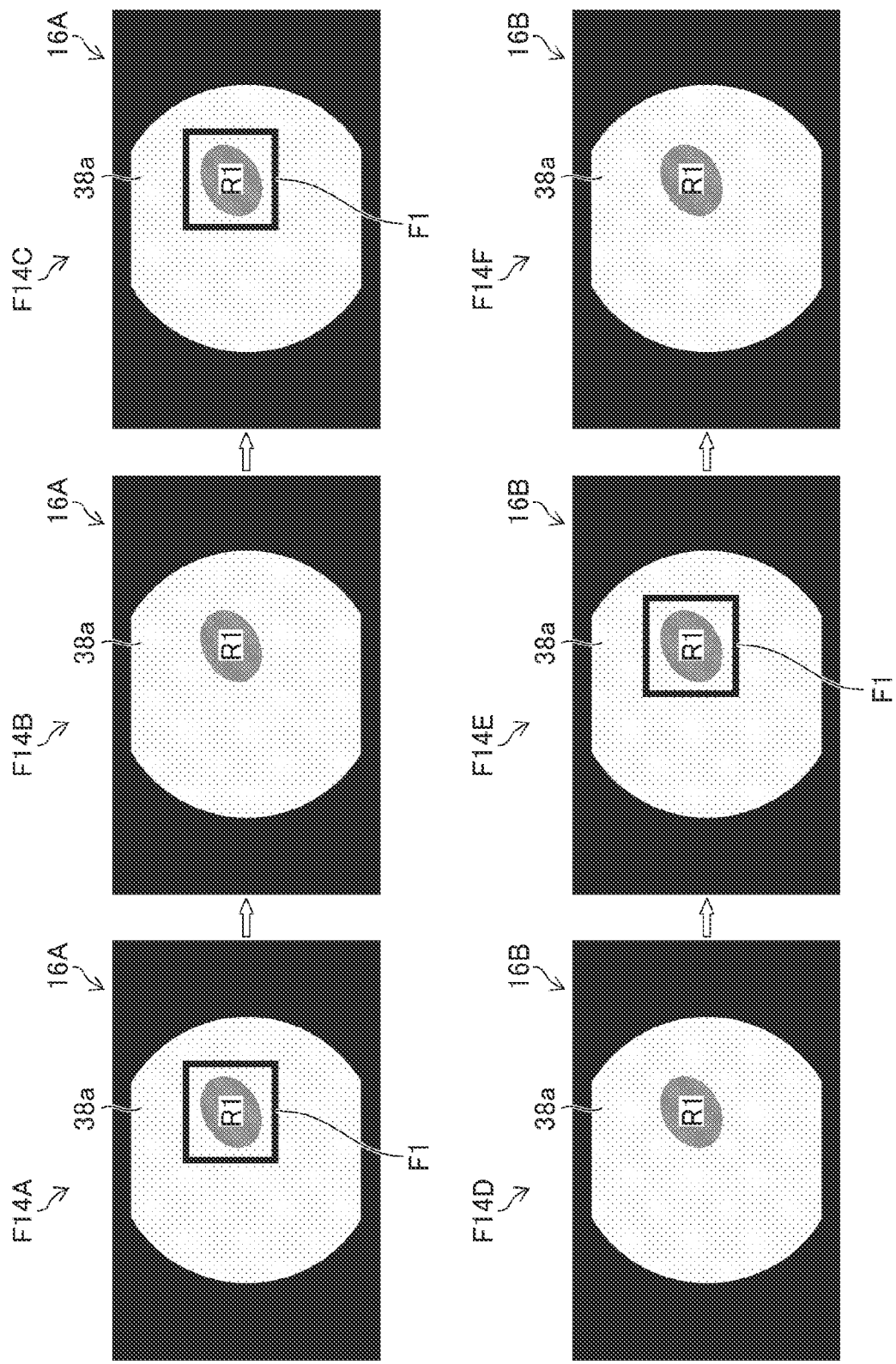
FIG. 14 is a diagram illustrating an example of transition of display on a first display and a second display.

FIG. 14 is a diagram illustrating an example of transition of display on the first display 16A and the second display 16B.

The reporting information display control unit 62B controls display on the first display 16A (an example of a first display unit) similarly to display on the display 16 according to the first embodiment. In FIG. 14, parts F14A, F14B, and F14C illustrate display on the first display 16A, which are similar to parts F4A, F4B, and F4C illustrated in FIG. 4.

That is, parts F14A and F14C each illustrate a case where reporting information is in a reporting state. In parts F14A and F14C, the frame-shaped figure F1 surrounding the region of interest R1 detected in the frame image 38a is superimposed on the frame image 38a. Part F14B illustrates a case where reporting information is in a non-reporting state. In part F14B, the figure F1 is not displayed, but only the frame image 38a is displayed.

The reporting information display control unit 62B changes, in accordance with a reporting state and a non-reporting state on the first display 16A, a manner in which the second display 16B (an example of a second display unit) displays the reporting information. Here, the reporting information display control unit 62B displays reporting information on the second display 16B when the reporting information is in a non-reporting state.

In FIG. 14, parts F14D, F14E, and F14F illustrate display on the second display 16B at the same timings as parts F14A, F14B, and F14C, respectively. The frame images 38a displayed in parts F14D, F14E, and F14F are the same as the frame images 38a displayed in parts F14A, F14B, and F14C, respectively.

In parts F14D and F14F, corresponding to the timings at which the reporting information is in a reporting state, the figure F1 is not displayed. On the other hand, in part F14E, corresponding to the timing at which the reporting information is in a non-reporting state, the frame-shaped figure F1 surrounding the region of interest R1 is superimposed on the frame image 38a.

In this way, reporting information is displayed on the second display 16B only when the reporting information is in a non-reporting state. Accordingly, in the first display 16A, it is possible to reduce an influence hindering observation by a user at the timing at which the reporting information is not necessary. In the second display 16B, the user is able to check the reporting information when the user needs the reporting information.

Here, the frame images 38a are displayed on the second display 16B. Alternatively, only the figure F1 as reporting information may be displayed on the second display 16B.

Figure 15:
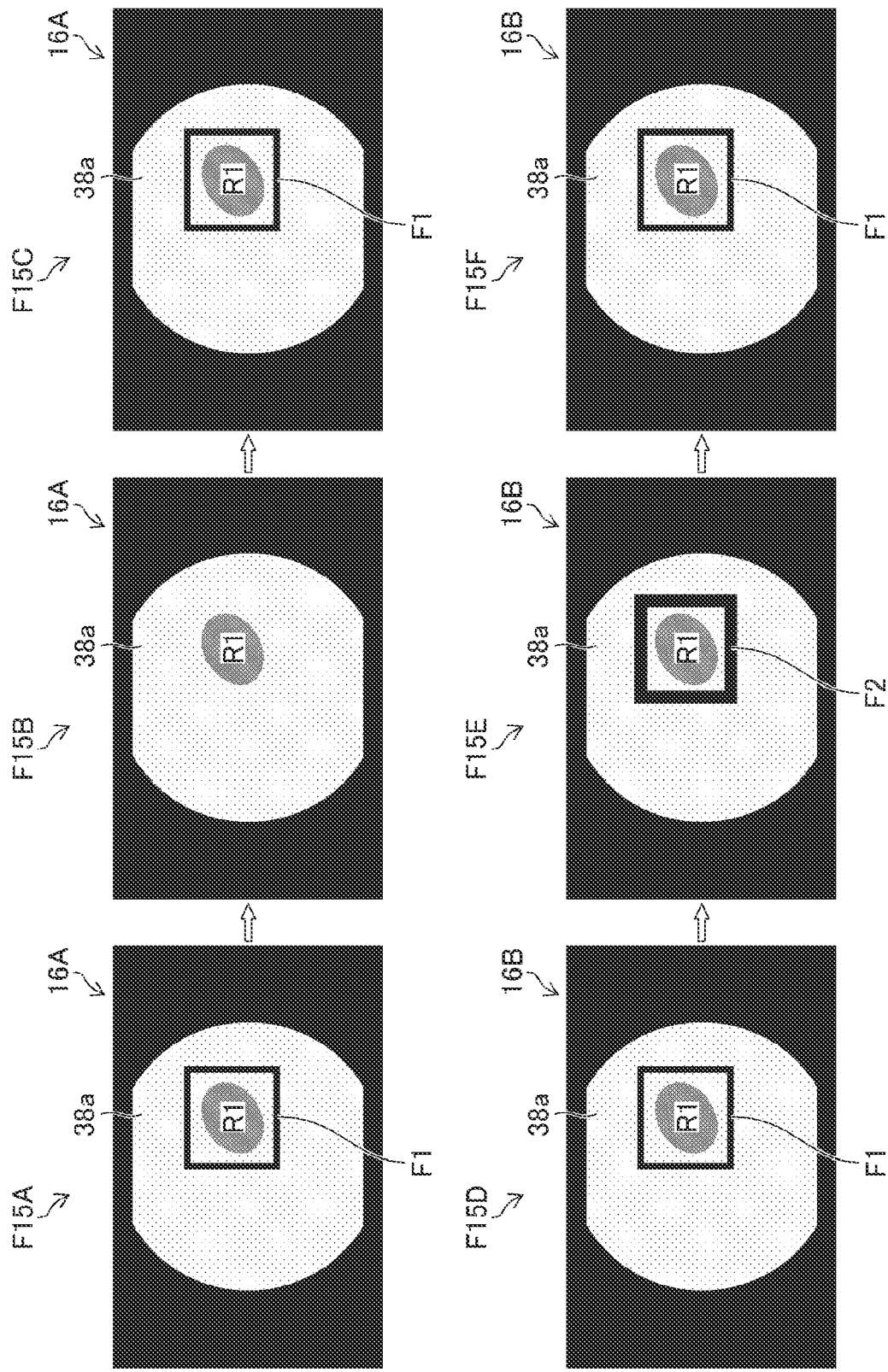
FIG. 15 is a diagram illustrating another example of transition of display on the first display and the second display.

FIG. 15 is a diagram illustrating another example of transition of display on the first display 16A and the second display 16B. In this example, the reporting information display control unit 62B increases an emphasis level of reporting information to be displayed on the second display 16B when the reporting information is in a non-reporting state. Here, the emphasis level is how easily a user can recognize the reporting information. The user is able to recognize the reporting information more easily as the emphasis level increases.

In FIG. 15, parts F15A, F15B, and F15C illustrate display on the first display 16A, which are similar to parts F14A, F14B, and F14C illustrated in FIG. 14. In FIG. 15, parts F15D, F15E, and F15F illustrate display on the second display 16B at the same timings as parts F15A, F15B, and F15C, respectively. The frame images 38a displayed in parts F15D, F15E, and F15F are the same as the frame images 38a displayed in parts F15A, F15B, and F15C, respectively.

In parts F15D and F15F, corresponding to the timings of a reporting state, as in parts F15A and F15C, the frame-shaped figure F1 surrounding the region of interest R1 detected in the frame image 38a is superimposed on the frame image 38a. In part F15E, corresponding to the timing of a non-reporting state, a frame-shaped figure F2 surrounding the region of interest R1 detected in the frame image 38a is superimposed on the frame image 38a. Here, the line of the figure F2 is thicker than the line of the figure F1. Thus, the emphasis level of the figure F2 is higher than the emphasis level of the figure F1.

As a result of controlling display on the second display 16B in this manner, a user is able to check reporting information more easily when the user needs the reporting information in a non-reporting state.

The reporting information display control unit 62B may cause the second display 16B to display the pieces of information IN1 to IN4 for reporting the region of interest illustrated in FIG. 5 to FIG. 8. The reporting information display control unit 62B may cause the second display 16B to display the pieces of information IN1 to IN4 only when the reporting information is in a non-reporting state. In this case, the image display control unit 62A may or may not display a medical image on the second display 16B.

Figure 16:
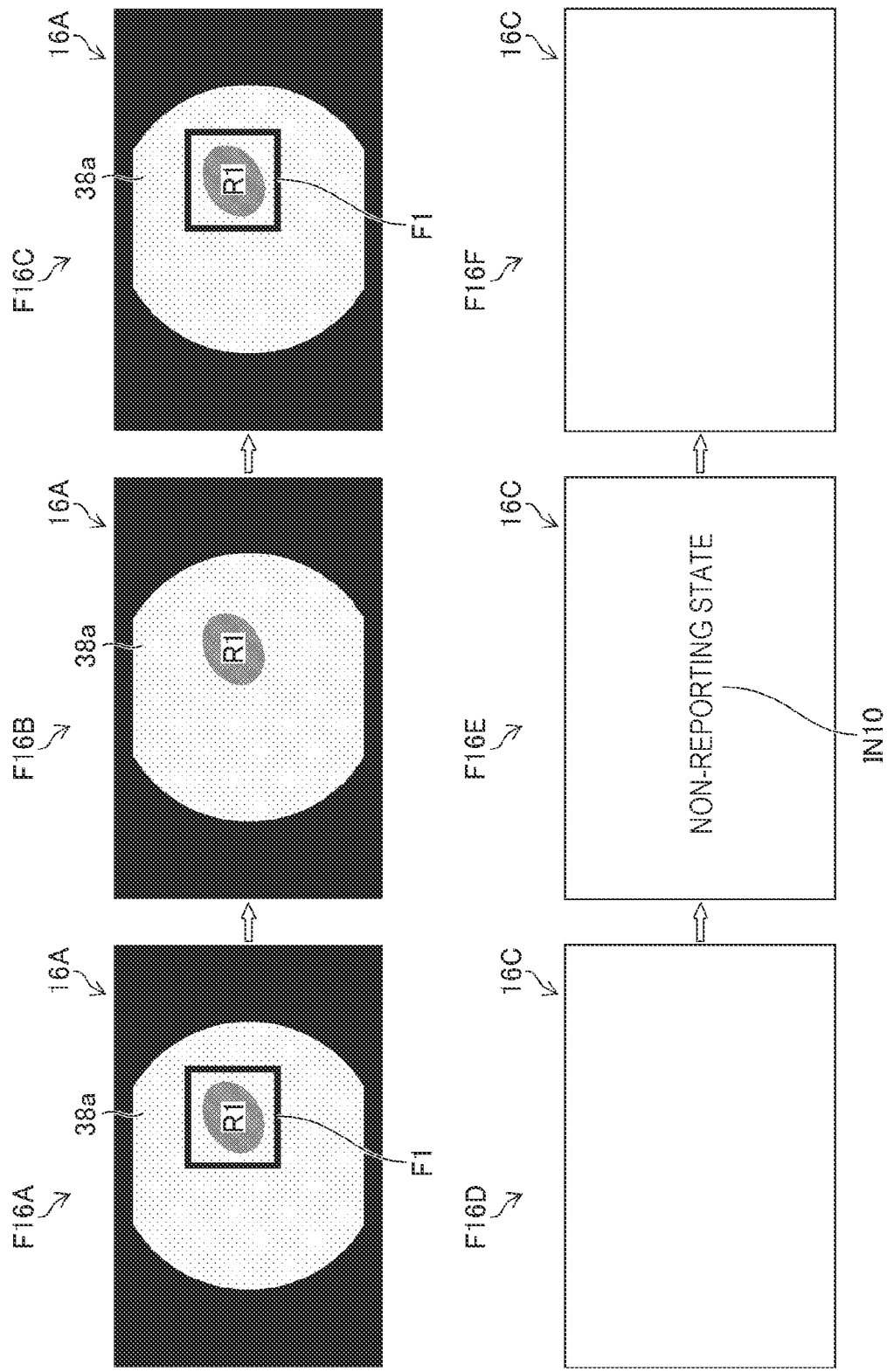
FIG. 16 is a diagram illustrating another example of transition of display on the first display and a third display.

FIG. 16 is a diagram illustrating another example of transition of display on the first display 16A and the third display 16C. In this example, the reporting information display control unit 62B displays information indicating that reporting information is in a non-reporting state on the third display 16C (an example of a third display unit) when the reporting information is in a non-reporting state.

In FIG. 16, parts F16A, F16B, and F16C illustrate display on the first display 16A, which are similar to parts F14A, F14B, and F14C illustrated in FIG. 14. In FIG. 16, parts F16D, F16E, and F16F illustrate display on the third display 16C at the same timings as parts F16A, F16B, and F16C, respectively.

The reporting information display control unit 62B causes the third display 16C to display nothing in parts F16D and F16F, corresponding to the timings of a reporting state. The reporting information display control unit 62B causes the third display 16C to display information IN10 indicating that reporting information is in a non-reporting state in part F16E, corresponding to the timing of a non-reporting state.

Here, characters are used as the information IN10. Alternatively, a symbol, a color, or the like may be used. In parts F16D and F16F, corresponding to the timings of a reporting state, the reporting information display control unit 62B may cause the third display 16C to display information indicating that reporting information is in a reporting state.

As a result of controlling display on the third display 16C in this manner, a user can recognize that reporting information is in a non-reporting state. In the non-report state, the user may perform an operation by using the operation unit 15 to immediately bring the first display 16A into a reporting state.

Figure 17:
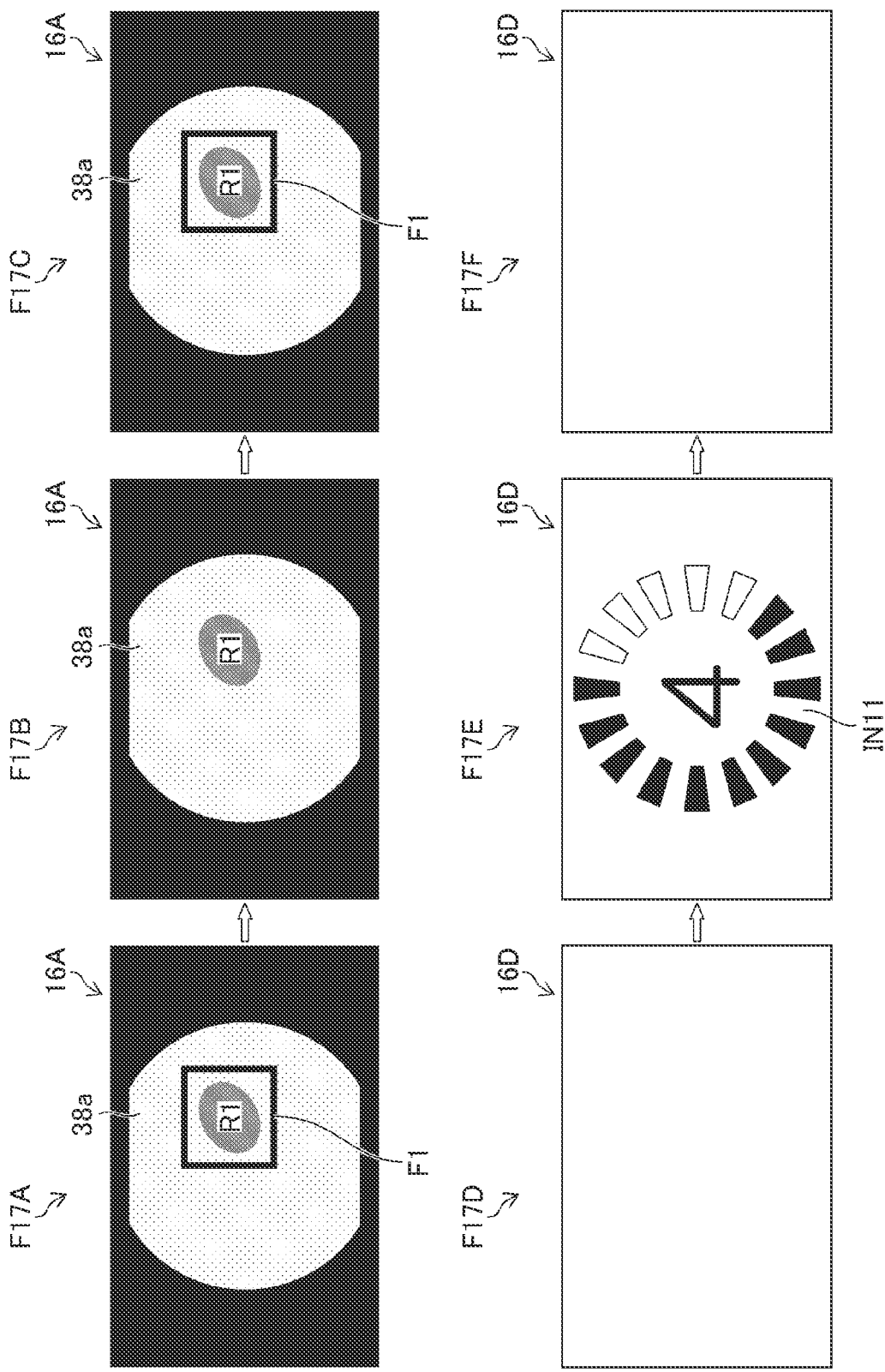
FIG. 17 is a diagram illustrating another example of transition of display on the first display and a fourth display.

FIG. 17 is a diagram illustrating another example of transition of display on the first display 16A and the fourth display 16D. In this example, the reporting information display control unit 62B causes the fourth display 16D (an example of a fourth display unit) to display information about a time elapsed from when the non-reporting condition is not satisfied.

In FIG. 17, parts F17A, F17B, and F17C illustrate display on the first display 16A, which are similar to parts F14A, F14B, and F14C illustrated in FIG. 14. Part F17B illustrates a case where reporting information is kept in a non-reporting state from when the frame image 38a does not satisfy the non-reporting condition to when the non-reporting time elapses. In FIG. 17, parts F17D, F17E, and F17F illustrate display on the fourth display 16D at the same timings as parts F17A, F17B, and F17C, respectively.

In parts F17D and F17F, corresponding to the timings at which the non-reporting condition is not satisfied, the reporting information display control unit 62B causes the fourth display 16D to display nothing. In part F17E, corresponding to the timing from when the frame image 38a does not satisfy the non-reporting condition to when the non-reporting time elapses, the reporting information display control unit 62B causes the fourth display 16D to display information IN11 indicating a remaining time during which the reporting information is to be in a non-reporting state, that is, indicating a difference between the non-reporting time and the elapsed time.

Here, text information indicating a remaining time during which the reporting information is to be in a non-reporting state, and a figure that indirectly represents the remaining time and in which the color of the region sequentially changes are displayed as the information IN11. Alternatively, a time elapsed from when the non-reporting condition is not satisfied may be displayed. In addition, the reporting information display control unit 62B may cause the second display 16B to display the pieces of information IN6 to IN9 indicating the remaining time illustrated in FIG. 9 to FIG. 12.

As a result of controlling display on the fourth display 16D in this manner, a user can recognize information about a time elapsed from when the non-reporting condition is not satisfied. In a state where the information IN11 is displayed on the fourth display 16D, the user may perform an operation by using the operation unit 15 to immediately bring the first display 16A into a reporting state.

Third Embodiment

Configuration of Medical Image Processing Apparatus

Figure 18:
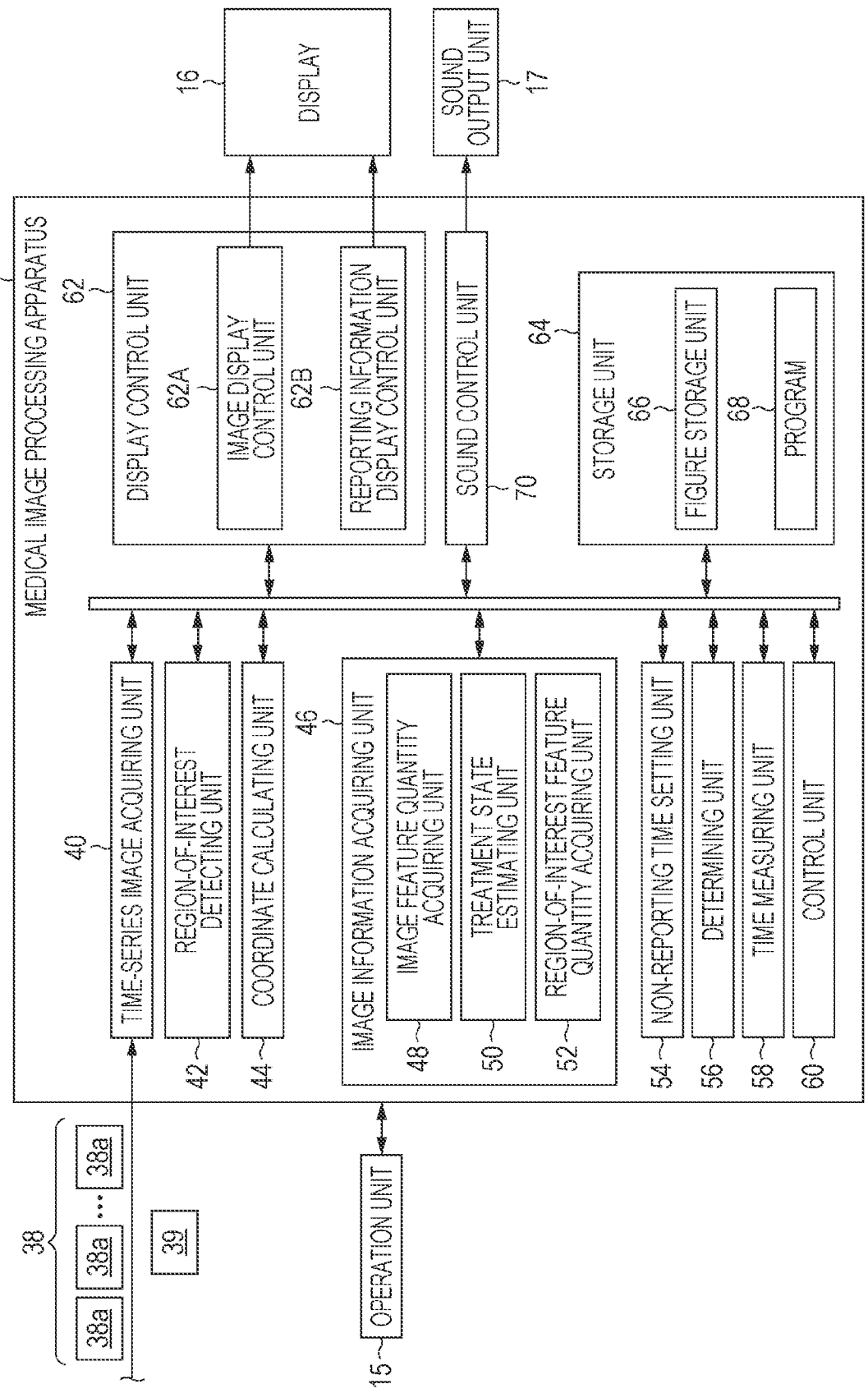
FIG. 18 is a block diagram illustrating an example of an electric configuration of a medical image processing apparatus.

FIG. 18 is a block diagram illustrating an example of an electric configuration of a medical image processing apparatus 14 according to a third embodiment. The parts common to those in the block diagram illustrated in FIG. 2 are denoted by the same reference numerals, and the detailed description thereof will be omitted.

The medical image processing apparatus 14 includes a sound control unit 70. The sound control unit 70 is an example of a reporting control unit that causes a reporting unit to report reporting information included in a medical image obtained through imaging of a subject. The sound control unit 70 is connected to a sound output unit 17. The sound output unit 17 functions as the reporting unit that reports reporting information and is included in the endoscope system 9 (see FIG. 1), for example. The sound output unit 17 includes a member that outputs a sound, such as a buzzer or a speaker. The sound control unit 70 causes the sound output unit 17 to output a sound in a reporting state to report reporting information. The sound to be output may be an alarm sound or a sound related to the reporting information.

Here, a description has been given of a configuration including the display 16 and the sound output unit 17 as a reporting unit that reports reporting information, but the configuration may include only the sound output unit 17. Alternatively, a lamp that emits light, a vibrator that vibrates, or the like may be used as a reporting unit that reports reporting information.

Others

The above-described medical image processing method can be configured as a program for causing a computer to implement individual steps, and it is possible to configure a non-transitory recording medium, such as a compact disc-read only memory (CD-ROM), storing the program.

In the embodiments described above, the endoscope processor apparatus 12 and the medical image processing apparatus 14 have been described as apparatuses different from each other. Alternatively, the endoscope processor apparatus 12 and the medical image processing apparatus 14 may be integrated together as the endoscope processor apparatus 12 having the function of the medical image processing apparatus 14.

The hardware structure of a processing unit that executes various processes of the endoscope processor apparatus 12 and the medical image processing apparatus 14 includes various types of processors described below. The various types of processors include a central processing unit (CPU), which is a general-purpose processor that executes software (program) and functions as various processing units; a graphics processing unit (GPU), which is a processor specializing in image processing; a programmable logic device (PLD), which is a processor whose circuit configuration is changeable after manufacturing, such as a field programmable gate array (FPGA); a dedicated electric circuit, which is a processor having a circuit configuration designed exclusively for executing specific processing, such as an application specific integrated circuit (ASIC), and the like.

A single processing unit may be constituted by one of these various types of processors or may be constituted by two or more processors of the same type or different types (for example, a combination of a plurality of FPGAs, a combination of a CPU and an FPGA, or a combination of a CPU and a GPU). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various types of processing units are constituted by using one or more of the above-described various types of processors as a hardware structure.

Furthermore, the hardware structure of these various types of processors is, more specifically, electric circuitry including a combination of circuit elements, such as semiconductor elements.

The technical scope of the present invention is not limited to the scope described in the above embodiments. The components in the individual embodiments can be appropriately combined between embodiments without deviating from the gist of the present invention.

REFERENCE SIGNS LIST 9 endoscope system
10 endoscope
11 light source apparatus
12 endoscope processor apparatus
13 display apparatus
14 medical image processing apparatus
15 operation unit
16 display
16A first display
16B second display
16C third display
16D fourth display
17 sound output unit
20 insertion section
21 handheld operation section
22 universal cord
25 soft part
26 bending part
27 distal end part 28 imaging device
29 bending operation knob
30 air/water supply button
31 suction button
32 still image capturing instruction unit
33 treatment tool port
35 light guide
36 signal cable
37a connector
37b connector
38 moving image
38a frame image
39 still image
40 time-series image acquiring unit
42 region-of-interest detecting unit
44 coordinate calculating unit
46 image information acquiring unit
48 image feature quantity acquiring unit
50 treatment state estimating unit
52 region-of-interest feature quantity acquiring unit
54 non-reporting time setting unit
56 determining unit
58 time measuring unit
60 control unit
62 display control unit
62A image display control unit
62B reporting information display control unit
64 storage unit
66 figure storage unit
68 program
70 sound control unit
F1, F2 figure
IN1 to IN11 information
R1 region of interest
S1 to S10 individual steps of medical image processing method

What is claimed is:

1. A medical image processing apparatus comprising one or more processors configured to:
perform control to bring reporting information included in a medical image into either a reporting state in which the reporting information is reported by one or more displays or a non-reporting state in which the reporting information is not reported by the one or more displays;
bring the reporting information into the non-reporting state in a case where the medical image satisfies a non-reporting condition and bring the reporting information into the reporting state after a non-reporting time has elapsed from when the medical image does not satisfy the non-reporting condition;
sequentially acquire frame images of the medical image;
acquire the reporting information from the medical image;
determine whether or not the medical image satisfies the non-reporting condition; and
measure a time elapsed from when the medical image does not satisfy the non-reporting condition.

2. The medical image processing apparatus according to claim 1,
wherein the non-reporting condition is a condition of determining an image feature quantity of the medical image,
wherein the one or more processors are configured to acquire the image feature quantity from the medical image.

3. The medical image processing apparatus according to claim 2, wherein the image feature quantity includes at least one of a luminance of the medical image, color information of the medical image, a temporal change in the medical image, or frequency information of the medical image.

4. The medical image processing apparatus according to claim 1,
wherein the non-reporting condition is a condition of determining a treatment state of a subject in the medical image,
wherein the one or more processors are configured to estimate the treatment state from the medical image.

5. The medical image processing apparatus according to claim 4, wherein the one or more processors are configured to set the non-reporting time in accordance with the treatment state.

6. The medical image processing apparatus according to claim 1,
wherein the non-reporting condition is a condition of determining a region-of-interest feature quantity,
wherein the one or more processors are configured to:
detect a region of interest from the medical image; and
acquire the region-of-interest feature quantity from the region of interest.

7. The medical image processing apparatus according to claim 6, wherein the region-of-interest feature quantity includes at least one of an area of the region of interest, a position of the region of interest in the medical image, or a temporal change in the region of interest.

8. The medical image processing apparatus according to claim 1, wherein
the one or more displays are configured to output a sound, and
the one or more processors are configured to cause the one or more displays to output the sound.

9. The medical image processing apparatus according to claim 1, wherein
the one or more displays includes a first display, and
the one or more processors are configured to cause the first display to display the reporting information.

10. The medical image processing apparatus according to claim 9, wherein the one or more processors are configured to cause a third display different from the first display to display information indicating the non-reporting state.

11. The medical image processing apparatus according to claim 9, wherein the one or more processors are configured to cause a fourth display different from the first display to display information about a time elapsed from when the medical image does not satisfy the non-reporting condition.

12. A diagnosis support apparatus comprising:
the medical image processing apparatus according to claim 9; and
the first display.

13. The medical image processing apparatus according to claim 9, wherein
the one or more displays includes a second display different from the first display, and
the one or more processors are configured to cause the second display to display the reporting information.

14. The medical image processing apparatus according to claim 13, wherein the one or more processors are configured to change, in accordance with the reporting state and the non-reporting state, a manner in which the second display displays the reporting information.

15. The medical image processing apparatus according to claim 14, wherein the one or more processors are configured to cause the second display to display the reporting information in a case of the non-reporting state.

16. A medical image processing method comprising:

performing control to bring reporting information included in a medical image into either a reporting state in which the reporting information is reported by one or more displays or a non-reporting state in which the reporting information is not reported by the one or more displays, bringing the reporting information into the non-reporting state in a case where the medical image satisfies a non-reporting condition and bringing the reporting information into the reporting state after a non-reporting time has elapsed from when the medical image does not satisfy the non-reporting condition;

sequentially acquiring frame images of the medical image;

acquiring the reporting information from the medical image;

determining whether or not the medical image satisfies the non-reporting condition; and measuring a time elapsed from when the medical image does not satisfy the non-reporting condition.

17. A non-transitory computer-readable recording medium storing instructions that, when read by a computer, cause the computer to execute the medical image processing method according to claim 16.

* * * * *